(12) United States Patent
Hereu et al.

(10) Patent No.: US 9,108,918 B2
(45) Date of Patent: Aug. 18, 2015

(54) PROCESS FOR PREPARING 5-(2-{[6-(2,2-DIFLUORO-2-PHENYLETHOXY)HEXYL]AMINO}-1(R)-HYDROXYETHYL)-8-HYDROXYQUINOLIN-2(1H)-ONE VIA A NOVEL INTERMEDIATE

(71) Applicants: Iolanda Marchueta Hereu, Sant Feliu de Llobrega (ES); Enrique Moyes Valls, Sant Feliu de Llobrega (ES)

(72) Inventors: Iolanda Marchueta Hereu, Sant Feliu de Llobrega (ES); Enrique Moyes Valls, Sant Feliu de Llobrega (ES)

(73) Assignee: ALMIRALL, S.A., Barcelona (ES)

( * ) Notice: Subject to any disclaimer, the term of this patent is extended or adjusted under 35 U.S.C. 154(b) by 0 days.

(21) Appl. No.: 14/350,108

(22) PCT Filed: Oct. 2, 2012

(86) PCT No.: PCT/EP2012/069475
§ 371 (c)(1),
(2) Date: Apr. 7, 2014

(87) PCT Pub. No.: WO2013/050375
PCT Pub. Date: Apr. 11, 2013

(65) Prior Publication Data
US 2015/0011769 A1      Jan. 8, 2015

Related U.S. Application Data

(60) Provisional application No. 61/561,645, filed on Nov. 18, 2011.

(30) Foreign Application Priority Data

Oct. 7, 2011   (EP) .................................. 11382316

(51) Int. Cl.
*C07D 215/26*   (2006.01)
*A61K 31/4704*   (2006.01)

(52) U.S. Cl.
CPC ........... *C07D 215/26* (2013.01); *A61K 31/4704* (2013.01)

(58) Field of Classification Search
CPC ........................ C07D 215/26; A61K 31/4704
See application file for complete search history.

(56) References Cited

U.S. PATENT DOCUMENTS

| | | | |
|---|---|---|---|
| 2,579,479 A | 12/1951 | Djerassi et al. |
| 2,837,464 A | 6/1958 | Nobile |
| 2,897,216 A | 7/1959 | Oliveto et al. |
| 3,007,923 A | 11/1961 | Muller et al. |
| 3,053,865 A | 9/1962 | Taub et al. |
| 3,104,246 A | 9/1963 | Amiard et al. |
| 3,134,718 A | 5/1964 | Nobile et al. |
| 3,134,719 A | 5/1964 | Ranchhordas et al. |
| 3,678,137 A | 7/1972 | Pfeiffer et al. |
| 3,929,768 A | 12/1975 | Brattsand et al. |
| 3,970,677 A | 7/1976 | Nishimura et al. |
| 3,975,391 A | 8/1976 | Nakagawa et al. |
| 3,983,233 A | 9/1976 | Brattsand et al. |
| 3,994,901 A | 11/1976 | Nakagawa et al. |
| 4,022,776 A | 5/1977 | Nakagawa et al. |
| 4,022,784 A | 5/1977 | Nakagawa et al. |
| 4,026,897 A | 5/1977 | Nakagawa et al. |
| 4,068,076 A | 1/1978 | Nakagawa et al. |
| 4,145,542 A | 3/1979 | Nakagawa et al. |
| 4,254,129 A | 3/1981 | Carr et al. |
| 4,254,130 A | 3/1981 | Carr et al. |
| 4,753,962 A | 6/1988 | Ainsworth et al. |
| 4,992,474 A | 2/1991 | Skidmore et al. |
| 4,997,986 A | 3/1991 | Mitchell et al. |
| 5,099,068 A | 3/1992 | Mitchell et al. |
| 5,109,023 A | 4/1992 | Mitchell et al. |
| 5,201,308 A | 4/1993 | Newhouse |
| 5,263,475 A | 11/1993 | Altermatt et al. |
| 5,283,262 A | 2/1994 | Mitchell et al. |
| 5,435,301 A | 7/1995 | Herold et al. |
| 5,482,934 A | 1/1996 | Calatayud et al. |
| 5,507,281 A | 4/1996 | Kuhnel et al. |

(Continued)

FOREIGN PATENT DOCUMENTS

DE   1 113 690   2/1958
DE   2 236 272   2/1973

(Continued)

OTHER PUBLICATIONS

U.S. Appl. No. 14/386,424, filed Sep. 19, 2014, Gemma Mestres Amat et al.

(Continued)

*Primary Examiner* — D M Seaman
(74) *Attorney, Agent, or Firm* — Finnegan, Henderson, Farabow, Garrett & Dunner, LLP

(57) ABSTRACT

The present invention is concerned with a process for preparing 5-(2{[6-(2,2-difluoro-2-phenylethoxy)hexyl]amino}-1(R)-hydroxyethyl)-8-hydroxyquinolin-2(1H)-one or a pharmaceutically acceptable salt thereof.

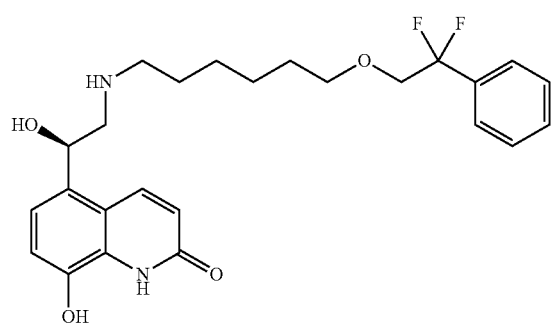

26 Claims, No Drawings

(56) References Cited

U.S. PATENT DOCUMENTS

| | | | |
|---|---|---|---|
| 5,617,845 A | 4/1997 | Poss et al. | |
| 5,648,370 A | 7/1997 | Bonnert et al. | |
| 5,685,294 A | 11/1997 | Gupte et al. | |
| 6,541,669 B1 | 4/2003 | Moran et al. | |
| 7,498,321 B2 | 3/2009 | Biggadike et al. | |
| 7,964,615 B2 | 6/2011 | Puig Duran et al. | |
| 8,178,679 B2 | 5/2012 | Matassa et al. | |
| 8,242,177 B2 | 8/2012 | Duran et al. | |
| 8,283,342 B2 | 10/2012 | Puig Duran et al. | |
| 8,420,669 B2 | 4/2013 | Puig Duran et al. | |
| 8,524,908 B2 * | 9/2013 | Marchueta Hereu et al. | 546/157 |
| 8,563,731 B2 | 10/2013 | Carrera et al. | |
| 2002/0055651 A1 | 5/2002 | Moran et al. | |
| 2003/0136405 A1 | 7/2003 | Goede et al. | |
| 2003/0153597 A1 | 8/2003 | Moran et al. | |
| 2004/0059116 A1 | 3/2004 | Moran et al. | |
| 2004/0167167 A1 | 8/2004 | Mammen et al. | |
| 2005/0043337 A1 | 2/2005 | Rito et al. | |
| 2005/0159448 A1 | 7/2005 | McKinnell et al. | |
| 2005/0192316 A1 | 9/2005 | Moran et al. | |
| 2005/0215590 A1 | 9/2005 | Brown et al. | |
| 2005/0272769 A1 | 12/2005 | Linsell | |
| 2006/0019991 A1 | 1/2006 | McKinnell et al. | |
| 2006/0035931 A1 | 2/2006 | Chao et al. | |
| 2006/0081246 A1 | 4/2006 | Goede et al. | |
| 2006/0178410 A1 | 8/2006 | Moran et al. | |
| 2006/0205949 A1 | 9/2006 | Dalziel et al. | |
| 2007/0197536 A1 | 8/2007 | Dal Piaz et al. | |
| 2009/0042933 A1 | 2/2009 | Duran et al. | |
| 2009/0082378 A1 | 3/2009 | Puig Duran et al. | |
| 2010/0093681 A1 | 4/2010 | Puig Duran et al. | |
| 2010/0168161 A1 | 7/2010 | Tañ et al. | |
| 2010/0324000 A1 | 12/2010 | Giulio Matassa et al. | |
| 2011/0028442 A1 | 2/2011 | Puig Duran et al. | |
| 2011/0251165 A1 | 10/2011 | Puig Duran et al. | |
| 2011/0251166 A1 | 10/2011 | Puig Duran et al. | |
| 2011/0251234 A1 | 10/2011 | Carrera Carrera et al. | |
| 2012/0004414 A1 | 1/2012 | Marchueta Hereu et al. | |
| 2012/0029014 A1 | 2/2012 | Ruf et al. | |
| 2012/0040941 A1 | 2/2012 | Ruf et al. | |
| 2014/0038928 A1 | 2/2014 | Ruf et al. | |
| 2014/0343097 A1 | 11/2014 | Ruf et al. | |
| 2015/0057256 A1 | 2/2015 | Amat et al. | |
| 2015/0065471 A1 | 3/2015 | Duran et al. | |

FOREIGN PATENT DOCUMENTS

| | | |
|---|---|---|
| DE | 2 323 215 | 11/1973 |
| DE | 2 310 140 | 9/1974 |
| DE | 24 61 861 | 8/1975 |
| DE | 41 29 535 | 3/1992 |
| DE | 42 39 402 A1 | 5/1994 |
| EP | 0 057 401 | 8/1982 |
| EP | 0 069 715 A1 | 1/1983 |
| EP | 0 147 719 A2 | 7/1985 |
| EP | 0 166 294 A2 | 1/1986 |
| EP | 0 286 242 A2 | 10/1988 |
| EP | 0 317 206 A2 | 5/1989 |
| EP | 0 424 790 A2 | 5/1991 |
| EP | 0 505 321 A2 | 9/1992 |
| EP | 0 674 533 B1 | 3/1999 |
| EP | 1 078 629 A2 | 2/2001 |
| EP | 1 235 787 B1 | 10/2003 |
| EP | 1 577 291 A1 | 9/2005 |
| ES | 2 232 306 A1 | 5/2005 |
| GB | 0 869 511 | 5/1961 |
| GB | 1 200 886 | 8/1970 |
| GB | 1 247 370 | 9/1971 |
| GB | 1 458 251 | 12/1976 |
| GB | 1 468 156 | 3/1977 |
| GB | 2 041 763 A | 9/1980 |
| GB | 2 140 800 A | 12/1984 |
| GB | 2 160 863 A | 1/1986 |
| GB | 2 165 159 A | 4/1986 |
| GB | 2 242 134 A | 9/1991 |
| JP | 51-149282 A | 12/1976 |
| JP | 59-093051 A | 5/1984 |
| WO | WO 91/02558 A1 | 3/1991 |
| WO | WO 91/14468 A1 | 10/1991 |
| WO | WO 92/00771 A1 | 1/1992 |
| WO | WO 92/03175 A1 | 3/1992 |
| WO | WO 92/04068 A1 | 3/1992 |
| WO | WO 92/04928 A2 | 4/1992 |
| WO | WO 92/09322 A1 | 6/1992 |
| WO | WO 96/32150 A1 | 10/1996 |
| WO | WO 96/35667 | 11/1996 |
| WO | WO 97/00703 A1 | 1/1997 |
| WO | WO 97/12687 A1 | 4/1997 |
| WO | WO 98/09632 A1 | 3/1998 |
| WO | WO 99/30703 A1 | 6/1999 |
| WO | WO 99/64035 A1 | 12/1999 |
| WO | WO 01/36375 A1 | 5/2001 |
| WO | WO 01/42193 A1 | 6/2001 |
| WO | WO 02/066422 A1 | 8/2002 |
| WO | WO 02/070490 A1 | 9/2002 |
| WO | WO 02/092606 A1 | 11/2002 |
| WO | WO 03/000325 A1 | 1/2003 |
| WO | WO 03/042160 A1 | 5/2003 |
| WO | WO 03/061742 A2 | 7/2003 |
| WO | WO 03/072539 A1 | 9/2003 |
| WO | WO 03/091204 A1 | 11/2003 |
| WO | WO 03/097613 A1 | 11/2003 |
| WO | WO 03/099764 A1 | 12/2003 |
| WO | WO 2004/011416 A1 | 2/2004 |
| WO | WO 2004/016578 A2 | 2/2004 |
| WO | WO 2004/058729 A1 | 7/2004 |
| WO | WO 2004/089892 A2 | 10/2004 |
| WO | WO 2004/106279 A2 | 12/2004 |
| WO | WO 2005/030678 A2 | 4/2005 |
| WO | WO 2005/040103 | 5/2005 |
| WO | WO 2005/042514 | 5/2005 |
| WO | WO 2005/049581 A1 | 6/2005 |
| WO | WO 2005/097804 | 10/2005 |
| WO | WO 2005/121065 A2 | 12/2005 |
| WO | WO 2005/123692 A1 | 12/2005 |
| WO | WO 2005/123693 A1 | 12/2005 |
| WO | WO 2006/023457 A1 | 3/2006 |
| WO | WO 2006/051375 A1 | 5/2006 |
| WO | WO 2006/122788 A1 | 11/2006 |
| WO | WO 2009/131932 | 11/2006 |
| WO | WO 2007/106016 | 9/2007 |
| WO | WO 2007/124898 A1 | 11/2007 |
| WO | WO 2007/146715 | 12/2007 |
| WO | WO 2008/046598 A1 | 4/2008 |
| WO | WO 2008/093188 | 8/2008 |
| WO | WO 2008/095720 A1 | 8/2008 |
| WO | WO 2008/135819 | 11/2008 |
| WO | WO 2009/026408 | 2/2009 |
| WO | WO 2009/026584 | 2/2009 |
| WO | WO 2009/032764 | 3/2009 |
| WO | WO 2009/068177 A1 | 6/2009 |
| WO | WO 2009/106351 A1 | 9/2009 |
| WO | WO 2010/072354 A1 | 7/2010 |
| WO | WO 2010/094483 A1 | 8/2010 |
| WO | WO 2010/094484 A1 | 8/2010 |
| WO | WO 2010/102831 | 9/2010 |
| WO | WO 2010/102831 A1 | 9/2010 |
| WO | WO 2013/050375 A1 | 4/2013 |
| WO | WO 2013/139712 | 9/2013 |
| WO | WO 2013/149959 | 10/2013 |

OTHER PUBLICATIONS

U.S. Appl. No. 14/389,843, filed Oct. 1, 2014, Carlos Puig Duran et al.

Berge, S.M. et al., "Pharmaceutical salts," Journal of Pharmaceutical Sciences, 1977, 66(1), pp. 1-19.

Chowdhury, B.A. et al., "The risks and benefits of indacaterol—The FDA's review," New England Journal of Medicine, 2011, 365(24), pp. 2247-2249.

Dahl, R. et al., "Efficacy of a new once-daily long-acting inhaled $\beta_2$-agonist indacaterol versus twice-daily formoterol in COPD," Thorax, 2010, 65, pp. 473-479.

(56) References Cited

OTHER PUBLICATIONS

Dixon A.E., "Long-acting β-agonists and asthma: The saga continues," Am. J. Resp. Criti. Care Med., 2011, 184, pp. 1220-1221.
English translation for DE1113690.
Feldman, G. et al., "Efficacy and safety of indacaterol 150 μg once-daily in COPD: a double-blind, randomised, 12-week study," Bio Med Central, 2010, 10(11), pp. 1-9.
International Search Report dated Jun. 25, 2013, for International Application No. PCT/EP2013/055488.
International Search Report dated May 13, 2013, for International Application No. PCT/EP2013/056786.
Jacobsen, J.R. et al., "A multivalent approach to the discovery of long-acting $\beta_2$-adrenoceptor agonists for the treatment of asthma and COPD," J. Bioorganic & Medicinal Chemistry Letters, 2012, 22, pp. 1213-1218.
Konzett H. et al., "Versuchsanorduung zu Untersuchungen an der Bronchialmuskulatur," Arch. Exp. Path. Pharmacol. 195, 1940, pp. 71-75.
Konzett, H. et al., "Versuchsanorduung zu untersuchungen an der bronchialmuskulatur," Arch. Exp. Path. Pharmacol. 195, 1940, pp. 71-75. English Translation.
Van Noord, J.A. et al., "24-hour Bronchodilation following a single dose of the novel β_2-agonist olodaterol in COPD." J. Pulmonary Pharmacology & Therapeutics, 2011, 24, pp. 666-672.
U.S. Appl. No. 14/048,344; Office Action dated Oct. 23, 2014.
International Search Report for International Application No. PCT/EP2012/089475, dated Oct. 25, 2012.
U.S. Appl. No. 11/920,561, filed Feb. 11, 2008, Puig Duran et al.
U.S. Appl. No. 12/298,131, filed Nov. 10, 2008, Puig Duran et al.
U.S. Appl. No. 12/444,935, filed May 14, 2009, Bach Taña et al.
U.S. Appl. No. 12/526,090, filed Oct. 8, 2009, Puig Duran et al.
U.S. Appl. No. 12/745,195, filed May 27, 2010, Giulio Matassa et al.
U.S. Appl. No. 12/919,134, filed Oct. 7, 2010, Puig Duran et al.
U.S. Appl. No. 13/141,156, filed Jun. 21, 2011, Carrera Carrera et al.
U.S. Appl. No. 13/094,163, filed Apr. 26, 2011, Puig Duran et al.
U.S. Appl. No. 13/202,020, filed Oct. 18, 2011, Ruf et al.
U.S. Appl. No. 13/202,025, filed Oct. 14, 2011, Ruf et al.
U.S. Appl. No. 13/255,621, filed Sep. 19, 2011, Marchueta Hereu et al.
U.S. Appl. No. 13/428,450, filed Mar. 23, 2012, Giulio Matassa et al.
U.S. Appl. No. 13/538,117, filed Jun. 29, 2012, Bach Taña et al.
U.S. Appl. No. 14/048,344, filed Oct. 8, 2013, Thorsten Ruf et al.
U.S. Appl. No. 14/225,849, filed Mar. 28, 2014, Thorsten Ruf et al.
Bateman, E.D. et al, "Global strategy for asthma management and prevention: GINA executive summary," Eur Resp J., 31(1):143-178 (2008).
Bastin, R.D. et al. "Salt Selection and Optimisation for Pharmaceutical New Chemical Entities," Organic Process Research and Development, 4(5):427-435 (2000).
Budesonide, Merck Index, Monograph No. 01468 (2012).
CAPLUS$^{SM}$ English Abstract of DE 2 236 272, Accession No. 1973:405128.
CAPLUS$^{SM}$ English Abstract of DE 2 310 140, Accession No. 1975:31115.
CAPLUS$^{SM}$ English Abstract of journal article by De Meglio, P. et al., Accession No. 1980:426036.
CAPLUS$^{SM}$ English Abstract of JP 51 149 282, Accession No. 1977:468184.
CAPLUS$^{SM}$ English Abstract of JP 59 093 051, Accession No. 1985:45790.
Ciclesonide, Merck Index, Monograph No. 02263 (2012).
Coleman, R.A. et al. "Novel and Versatile Superfusion System: Its Use in the Evolution of Some Spasmogenic and Spasmolytic Agents Using Guinea-pig Isolated Tracheal Smooth Muscle," Journal of Pharmacological Methods, 21:71-86 (1989).
Cortijo, J. et al. "Effects of dantrolene on the responses to methylxanthines in the isolated guinea-pig trachea," European Journal of Pharmacology, 198:171-176 (1991).

Curran, P.K. et al. "Endogenous $\beta_3$- But Not $\beta_1$-Adrenergic Receptors are Resistant to Agonist-Mediated Regulation in Human SK-N-MC Neurotumor Cells," Cell. Signal., 8(5):355-364 (1996).
De Meglio, P. et al. "Synthesis and pharmacological study of orciprenaline and salbutamol derivatives," Farmaco, Edizione Scientifica, 35(3): 203-230 (1980).
De Vires, F. et al. "Use of β2 Agonists and Rsk of Acute Myocardial Infarction in Patients with Hypertension," Brit. J. Clin. Pharmacol. 65:580:586, 2008.
Deyrup, M.D. et al. "Structure-affinity profile of 8-hydroxycarbostyril-based agonists that dissociate slowly from the $\beta_2$-adrenoceptor," Naunyn-Schmiedeberg's Archives of Pharmacology, 359:168-177(1999).
Dexamethasone, Merck Index, Monograph No. 02943 (2011).
English Abstract of WO 2002/92606, Accession No. 00958733, 2 pp. (Nov. 21, 2002).
Furuie, H. et al. "Suppressive effect of novel phosphodiesterase4 (PDE4) inhibitor ONO-6126 on TNF-α release was increased after repeated oral administration in healthy Japanese subjects," 13$^{th}$ ERS Annual Congress, Sep. 27, 2003, Vienna. Eur. Resp. Journal, 22(Supp. 45):Abstract 2557 (2003).
Han "Advances in Characterization of Pharmaceutical Hydrates," Trends in Bio/Pharmaceutical Industry, 2(3):25-29 (2006).
Hart, D.J. "A Synthesis of (±)-Gephyrotoxin," Journal of Organic Chemistry, 46:3576-3578 (1981).
Hart, D.J. et al. "Total Syntheses of dl-Gephyrotoxin and dl-Dihydrogephyrotoxin," J. Am. Chem. Soc., 105(5):1255-1263 (1983).
Hashima, H. et al. "Synthesis and Biological Activities of the Marine Byrozoan Alkaloids Convolutamines A, C and F, and Lutamides A and C," Bioorganic & Medicinal Chemistry, 8:1757-1766 (2000).
Hett, R. et al. "Enantioselective Synthesis of Salmeterol via Asymmetric Borane Reduction," Tetrahedron Letters, 35(50):9375-9378 (1994).
Hett, R. et al. "Large-Scale Synthesis of Enantio- and Diastereomerically Pure (R,R)-Formoterol," Organic Process Research & Development, 2(2):96-99 (1998).
International Search Report mailed Sep. 12, 2006, for International Application No. PCT/EP2006/004680 (WO 2006/122788 A1).
International Search Report mailed Apr. 21, 2009, for International Application No. PCT/EP2009/001431 (WO 2009/106351).
International Search Report mailed Jun. 21, 2007, for International Application No. PCT/EP2007/003601 (WO 2007/124898 A1).
International Search Report mailed Mar. 19, 2008, for International Application No. PCT/EP2007/008992 (WO 2008/046598 A1).
International Search Report mailed Mar. 2, 2010, for International Application No. PCT/EP2009/008970 (WO 2010/072354).
International Search Report mailed Sep. 16, 2010, for International Application No. PCT/EP2010/001582 (WO 2010/102831).
International Search Report mailed May 27, 2010, for International Application No. PCT/EP2010/001026 (WO 2010/094483).
International Search Report mailed May 25, 2010, for International Application No. PCT/EP2010/001027 (WO 2010/094484).
International Search Report mailed May 28, 2008, for International Application No. PCT/EP2008/000975 (WO 2008/095720).
International Search Report mailed May 7, 2009, for International Application No. PCT/EP2008/009469 (WO 2009/068177).
Ismail, F.M.D. "Important fluorinated drugs in experimental and clinical use," Journal of Fluorine Chemistry 118:27-33 (2002).
Johnson, M. "Salmeterol," Medicinal Research Reviews, 15(3):225-257 (1995).
Kaiser, C. et al. "Adrenergic Agents. 1. Synthesis and Potential β-Adrenergic Agonist Activity of Some Catecholamine Analogs Bearing a Substituted Amino Functionality in the Meta Position," J. Med. Chem., 17(1):49-57 (1974).
Kikkawa, H. et al. "Differential contribution of two serine residues of wild type and constitutively active $\beta_2$-adrenoreceptors to the interaction with $\beta_2$-selective agonists," British Journal of Pharmacology, 121:1059-1064 (1997).
Meyers, A.I. et al. "Oxazolines. XI. Synthesis of Functionalized Aromatic and Aliphatic Acids. A Useful Protecting Group for Carboxylic Acids against Grignard and Hydride Reagents," J. Org. Chem., 39(18): 2787-2793 (1974).

(56) References Cited

OTHER PUBLICATIONS

Meyers, A.I. et al. "Substitutions on 1-Methoxynaphthalenes via their Oxazoline Derivatives: A Convenient Route to 1-Substituted Naphthoic Acids," *Synthesis Communications*, 2:105-107 (1983).
Mometasone, Merck Index, Monograph No. 06241 (2012).
Morissette, S.L. et al. "High-Throughput Crystallization: Polymorphs, Salts, Co-Crystals and Solvates of Pharmaceutical Solids," *Advanced Drug Delivery Reviews*, 56:275-300 (2004).
Murase, K. et al. "New β-Adrenoreceptor Stimulants. Studies on 3-Acylamino-4-hydroxy-α-(N-substituted aminomethyl)benzyl Alcohols," *Chem. Pharm. Bull.*, 25(6):1368-1377 (1977).
Nielsen, K.G. et al. "Flow-dependent effect of formoterol dry-powder inhaled from the Aerolizer®," *Eur. Respir. J.*, 10:2105-2109 (1997).
Patani, G.A. et al. "Bioisosterism: A Rational Approach in Drug Design," *Chem. Rev.* 96:3147-3176 (1996).
Portoghese, P.S. "Stereochemical Studies on Medicinal Agents. 19. X-Ray Crystal Structures of Two (±)-Allylprodine Diastereomers. The Role of the Allyl Group in Conferring High Stereoselectivity and Potency at Analgetic Receptors," *J. Med. Chem.*, 19(1):55-57 (1976).
Prednisone, Merck Index, Monograph No. 07722 (2012).
Quanjer Ph.H. et al. "Lung Volumes and Forced Ventilatory Flows," Eur Resp J., 6(Suppl16):5-40 (1993).
Salpeter S.R. et al., "Cardiovascular Effects of β-Agonists in Patients with Asthma and COPD: A Meta-Analysis" Chest, vol. 125, pp. 2309-2321 (2004).
Silverman, R.B. "The Organic Chemistry of Drug Design and Drug Action," Academic Press, Chapter 2, pp. 10-23 (1992).
Smart, B.E. "Fluorine substituent effects (on bioactivity)," *Journal of Fluorine Chemistry* 109:3-11 (2001).
Sterling, J. et al. "Novel Dual Inhibitors of AChE and MAO Derived from Hydroxy Aminoindan and Phenethylamine as Potential Treatment for Alzheimer's Disease," *J. Med. Chem.* 45(24):5260-5279 (2002).
STN Search Report, File CAPLUS, Accession No. 2003:875242 (2011).
Svenson, R. et al. "On the Hydrozirconation of Some Long-Chain Unsaturated Fatty Acid Oxazolines," *Chemica Scripta.* 19:149-153 (1982).
Vippagunta, SR et al. "Crystalline Solids," *Advanced Drug Delivery Reviews* 48:3-26 (2001).
Williams, D.A. et al. (eds.) *FOYE's Principles of Medicinal Chemistry*. 5th Edition, Lippincott Williams & Wilkins, 2002; pp. 59-63.
Yang, Z. "Synthesis of new α,α,β,β-tetrafluoroesters," *Journal of Fluorine Chemistry* 125:763-765 (2004).
Yang, Z. et al. "A Novel and Practical Method for the Preparation of α,α-Difluoro Functionalized Esters," *J. Chem. Soc., Chem. Commun.* 3:233-234 (1992).
Yoshizaki, S. et al. "Sympathomimetic Amines Having a 3,4-Dihydrocarbostyril Nucleus," *Chemical and Pharmaceutical Bulletin* 26(5):1611-1614 (1978).
Yoshizaki, S. et al. "Sympathomimetic Amines Having a Carbostyril Nucleus," *J. Med. Chem.* 19(9):1138-1142 (1976).

U.S. Appl. No. 11/920,561: Restriction Requirement dated Mar. 16, 2010.
U.S. Appl. No. 11/920,561: Office Action dated Jun. 2, 2010.
U.S. Appl. No. 11/920,561: Interview Summary dated Jun. 11, 2010.
U.S. Appl. No. 11/920,561: Office Action (Quayle Action) dated Nov. 9, 2010.
U.S. Appl. No. 11/920,561: Notice of Allowance dated Jan. 26, 2011.
U.S. Appl. No. 12/298,131: Office Action dated Apr. 25, 2011.
U.S. Appl. No. 12/298,131: Office Action dated Jan. 26, 2012.
U.S. Appl. No. 12/444,935: Restriction Requirement dated May 13, 2011.
U.S. Appl. No. 12/444,935: Office Action dated Jul. 7, 2011.
U.S. Appl. No. 12/444,935: Office Action dated Jan. 30, 2012.
U.S. Appl. No. 12/444,935: Office Action (Advisory Action) dated Jun. 4, 2012.
U.S. Appl. No. 12/745,195: Restriction Requirement dated Jan. 5, 2011.
U.S. Appl. No. 12/745,195: Office Action dated Mar. 9, 2011.
U.S. Appl. No. 12/745,195: Office Action dated Jul. 15, 2011.
U.S. Appl. No. 12/745,195: Notice of Allowance dated Dec. 28, 2011.
U.S. Appl. No. 13/094,156: Restriction Requirement dated Dec. 29, 2011.
U.S. Appl. No. 13/094,156: Office Action (Quayle Action) dated Feb. 14, 2012.
U.S. Appl. No. 13/094,156, Notice of Allowance dated Apr. 18, 2012.
U.S. Appl. No. 13/094,163: Office Action (Restriction Requirement) dated Jul. 6, 2012.
U.S. Appl. No. 13/094,163: Office Action dated Aug. 20, 2012.
U.S. Appl. No. 13/094,163: Notice of Allowance dated Dec. 12, 2012.
U.S. Appl. No. 12/745,195: Interview Summary dated Feb. 22, 2012.
U.S. Appl. No. 12/745,195: Notice of Allowance dated Feb. 24, 2012.
U.S. Appl. No. 12/526,090: Restriction Requirement dated Jul. 20, 2011.
U.S. Appl. No. 12/526,090: Office Action dated Oct. 14, 2011.
U.S. Appl. No. 12/526,090: Office Action dated Apr. 24, 2012.
U.S. Appl. No. 12/526,090: Interview Summary dated Jun. 26, 2012.
U.S. Appl. No. 12/526,090: Notice of Allowance dated Jun. 26, 2012.
U.S. Appl. No. 13/141,156 Notice of Allowance dated Jun. 21, 2013.
U.S. Appl. No. 13/202,020: Restriction Requirement dated Oct. 2, 2012.
U.S. Appl. No. 13/202,020: Office Action dated Apr. 8, 2013.
U.S. Appl. No. 14/048,344: Restriction Requirement dated Feb. 27, 2014.
U.S. Appl. No. 13/202,025: Restriction Requirement dated Oct. 4, 2012.
U.S. Appl. No. 13/202,025: Office Action dated Apr. 17, 2013.
U.S. Appl. No. 13/202,025: Office Action dated Oct. 1, 2013.
U.S. Appl. No. 13/202,025: Interview Summary dated Mar. 10, 2014.
U.S. Appl. No. 13/255,621: Notice of Allowance dated May 10, 2013.
U.S. Appl. No. 14/389,843: Restriction Requirement dated Jan. 2, 2015.

\* cited by examiner

PROCESS FOR PREPARING 5-(2-{[6-(2,2-DIFLUORO-2-PHENYLETHOXY)HEXYL]AMINO}-1(R)-HYDROXYETHYL)-8-HYDROXYQUINOLIN-2(1H)-ONE VIA A NOVEL INTERMEDIATE

This application is a national stage filing under 35 U.S.C. §371 of International Application No. PCT/EP2012/069475, filed on Oct. 2, 2012, which claims priority of European Patent Application No. 11382316.5, filed on Oct. 7, 2011, and also claims priority of U.S. Provisional Patent Application No. 61/561,645, filed on Nov. 18, 2011. The contents of these applications are each incorporated herein by reference.

The present invention is directed to novel processes for preparing 5-(2-{[6-(2,2-difluoro-2-phenylethoxy)hexyl]amino}-1(R)-hydroxyethyl)-8-hydroxyquinolin-2(1H)-one (Compound (I)) and pharmaceutically acceptable salts thereof. The present invention is also directed to intermediate compounds and to processes for preparing said intermediate compounds.

5-(2-{[6-(2,2-difluoro-2-phenylethoxy)hexyl]amino}-1(R)-hydroxyethyl)-8-hydroxyquinolin-2(1H)-one (Compound (I)) as well as a process for its manufacture are described in WO 2006/122788 and WO 2010/102831.

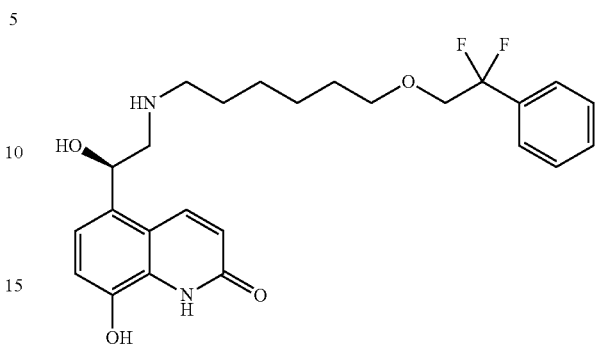

(I)

WO 2008/095720 discloses a method for preparing the napadisylate salt compound of formula (Ia).

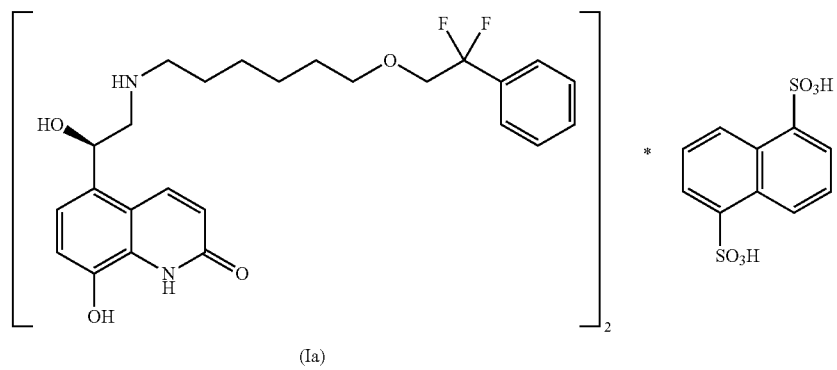

(Ia)

WO 2010/102831 describes an improved process for preparing compounds of formula (Ia), by selecting specific solvents and also by modifying or removing some purification steps, thus reducing the reaction time while obtaining the final product within higher yields and minimizing the amounts of impurities.

The synthetic process described in the above patent applications can be summarized in Scheme 1.

Scheme 1

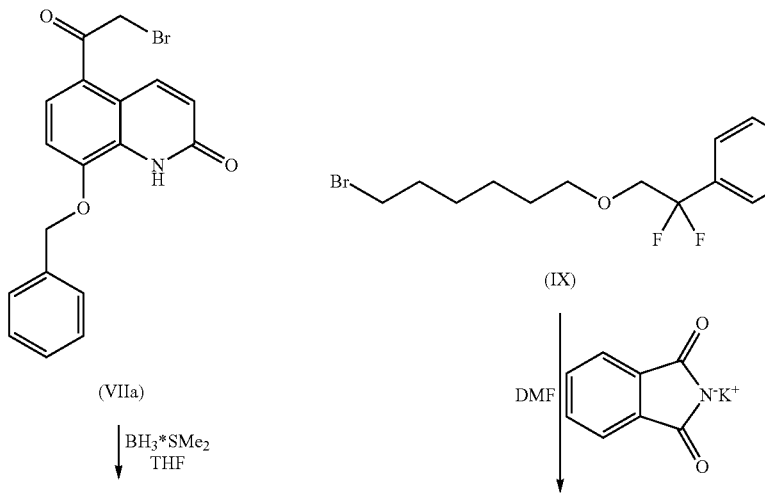

-continued
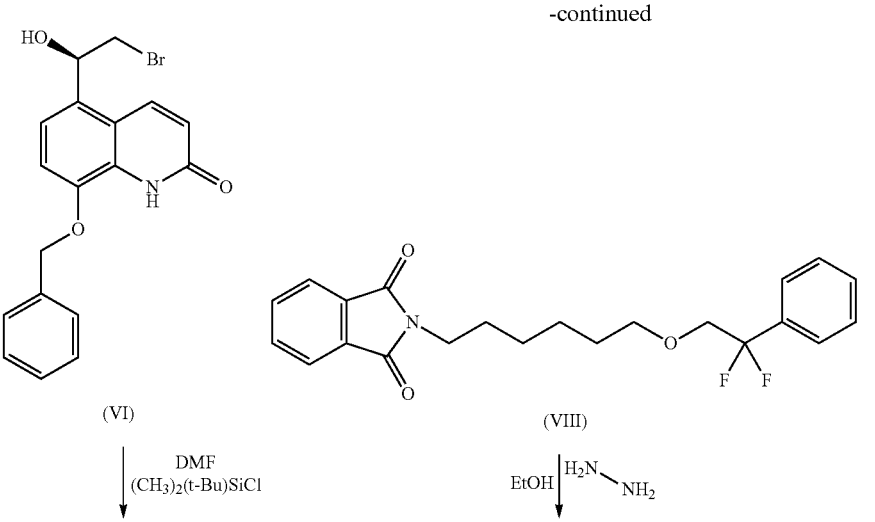
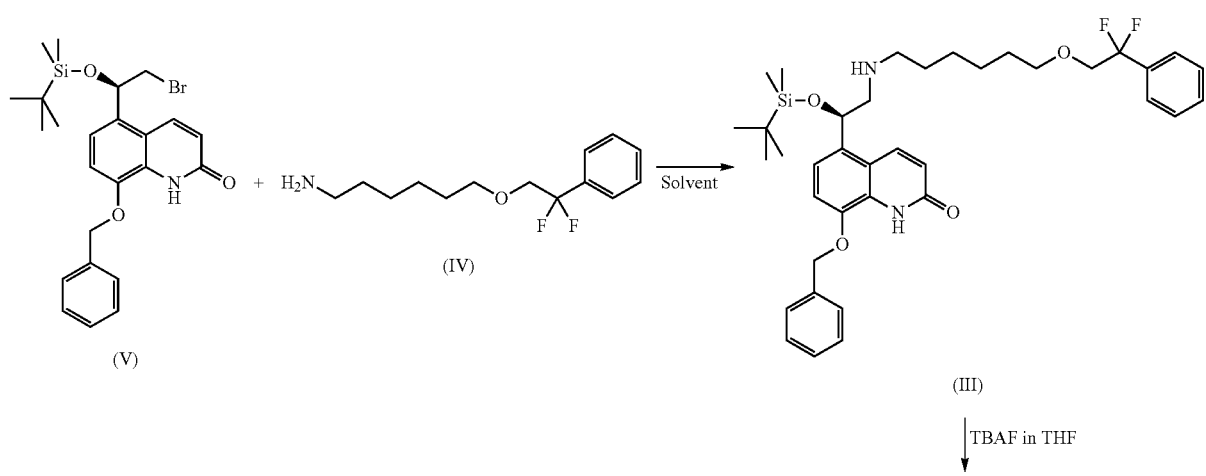
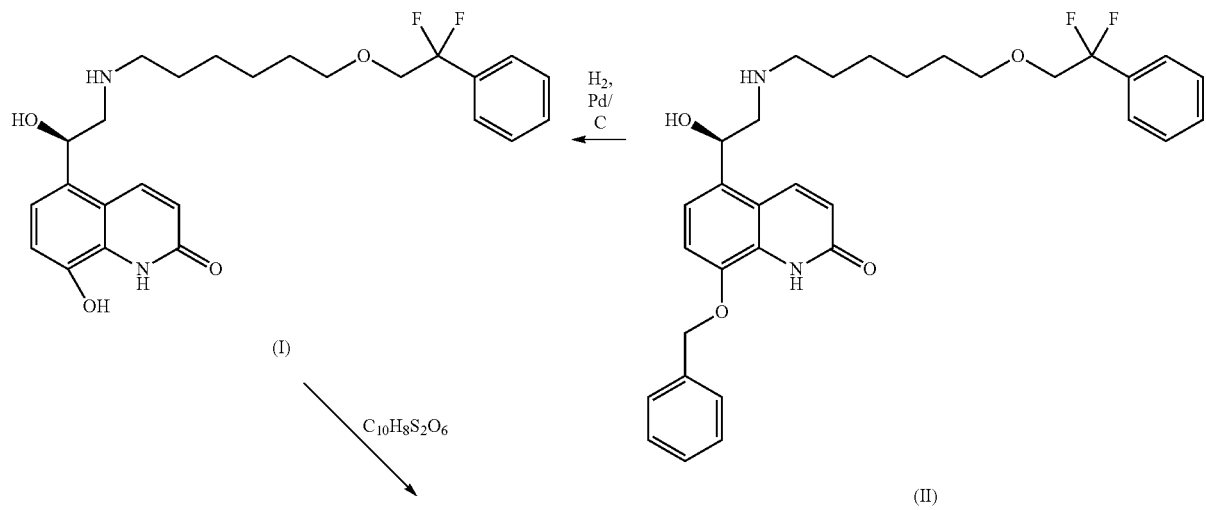

-continued

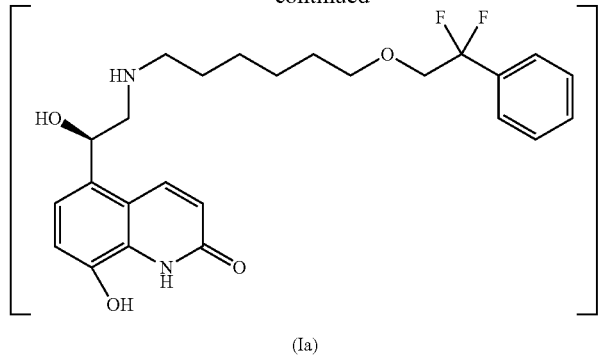 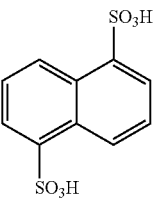

(Ia)

Therefore, in order to prepare compounds of formula (Ia), an alkylation reaction process of amine derivative of formula (IV) with the protected bromohydrin derivative of formula (V) is first carried out to give intermediates of formula (III), which are subsequently deprotected twice to give the compound of formula (I). The treatment of compound (I) with a pharmaceutically acceptable acid gives the corresponding salt compound of formula (Ia).

Intermediate of formula (IV) can be obtained by reacting intermediate of formula (VIII) with hydrazine, which is known to be a very toxic compound, in a solvent such as methanol, ethanol or tetrahydrofuran and at a temperature ranging from 50 to 90° C. Intermediate of formula (VIII) may be prepared reacting intermediate of formula (IX) with potassium phatalimide in a solvent such as dimethylformamide, dimethylsulfoxide or acetonitrile. These synthetic methods are already known and are described, for example, in WO 2006/122788 (Intermediates 8 and 9).

The protected bromohydrin derivative of formula (V) can be obtained by reducing the bromoketone derivative of formula (VIIa) using borane dimethylsulfide complex (BH$_3$-Me$_2$S), followed by protecting the hydroxyl moiety of intermediate (VI) using a suitable protecting group such as tert-butyldimethylsilyl chloride (TBS). These synthetic methods are already known and are described, for example, in US2004059116 (Example 9C), WO 2004/011416 (Example 2) and WO 2004/016578 (Example 1ii).

It is known that the borane dimethylsulfide complex gives rise to better enantiomeric purities contrary to other borane-based reagents which are known to yield poorer enantiomeric excess. However the borane dimethylsulfide complex, when used in this kind of the process, generates a high quantity of toxic and environmentally problematic by-products (dimethyl sulphide). Thus, it is highly recommended to avoid the use of this kind of reagents, especially at an industrial scale.

On the other hand, the deprotection process of intermediate (III) as depicted in Scheme 1 is carried out in two separate steps. The first deprotection step allows the formation of intermediates of formula (II) which are know to be very active compound due to their highly potent beta adrenergic activity and therefore should be handled using special equipments.

Furthermore, the above processes involve many steps of synthesis, including protection and deprotection reactions, and the need of many purification steps and/or separations of the intermediates between each steps and also the use of large quantities of solvents and catalyst thus rending the whole process very complicated and not adequate at industrial scales.

Therefore there is still a need to improve the above-mentioned synthetic process in order to produce compound (I), or its pharmaceutically acceptable salt, on an acceptable industrial scale in a shorter and a simpler synthetic process. The attention is especially drawn to intermediate (V), in particular to the reduction process of the bromoketone intermediate (VIIa) which reaction conditions are difficult to be effected and thus intermediate (VI) are difficult to obtain and to isolate with an adequate purity. In addition to this, it is convenient avoiding the manipulation of highly potent intermediates, such as intermediate (II), during the process, due to their active center which allow these intermediates to be highly active compounds.

It is therefore an object of the present invention to provide new synthetic processes and intermediate products suitable for the production of a compound of formula (I) or its pharmaceutically acceptable salts, which can be easily produced in a simplest way using industrially readily obtainable starting materials and avoiding the use of substances which are not environmental friendly.

Accordingly, the present invention is directed to a compound of formula (Ap) or a pharmaceutically acceptable salt thereof,

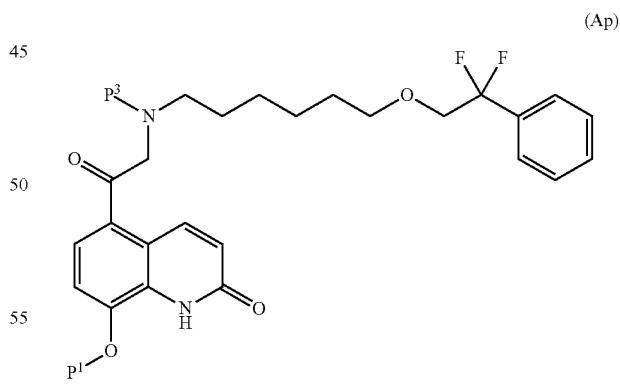

(Ap)

wherein $P^1$ represents a hydroxy protecting group and $P^3$ represents an amino protecting group.

The present invention further provides a process for preparing a compound of formula (Ap) or a pharmaceutically acceptable salt thereof, which process comprises a) reacting an intermediate of formula (VII)

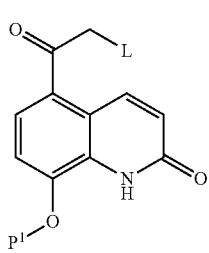

(VII)

wherein L is a leaving group, with a 6-(2,2-difluoro-2-phenylethoxy)hexan-1-amine derivative of formula (X),

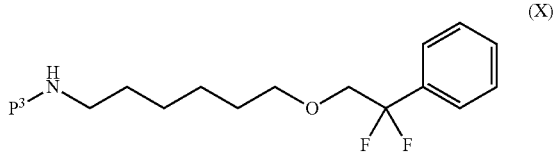

(X)

in the presence of a base, wherein $P^1$ and $P^3$ are as defined herein.

The invention further provides a process for preparing a 5-(2-{[6-(2,2-difluoro-2-phenylethoxy)hexyl]amino}-1(R)-hydroxyethyl)-8-hydroxyquinolin-2(1H)-one compound of formula (I) or a pharmaceutically acceptable salt thereof,

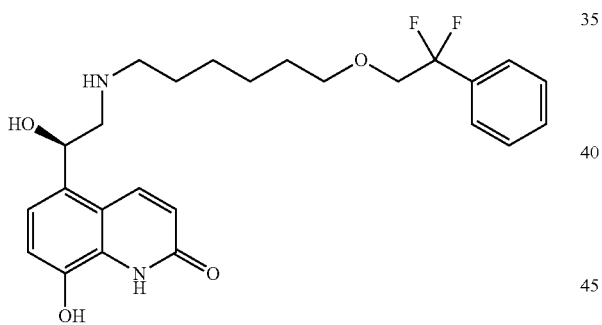

(I)

which process comprises reducing and deprotecting a compound of formula (Ap), or a pharmaceutically acceptable salt thereof, to give a compound of formula (I) or a pharmaceutically acceptable salt thereof.

The invention further provides:

a process for preparing a 5-(2-{[6-(2,2-difluoro-2-phenylethoxy)hexyl]amino}-1(R)-hydroxyethyl)-8-hydroxyquinolin-2(1H)-one compound of formula (I) or a pharmaceutically acceptable salt thereof, which comprises (i) preparing a compound of formula (Ap) or a pharmaceutically acceptable salt thereof by a process of the invention, and then (ii) reducing and deprotecting the compound of formula (Ap), or a pharmaceutically acceptable salt thereof, by a process of the invention, to give a compound of formula (I) or a pharmaceutically acceptable salt thereof;

a compound of formula (A1) or a pharmaceutically acceptable salt thereof;

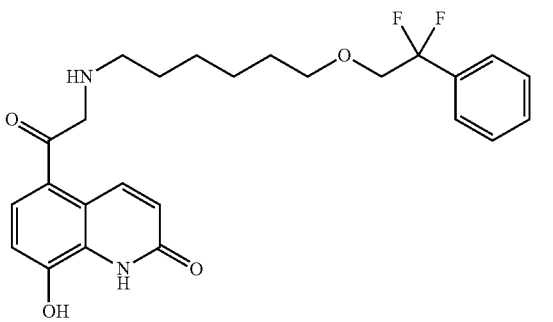

(A1)

a compound of formula (Bp) or a pharmaceutically acceptable salt thereof

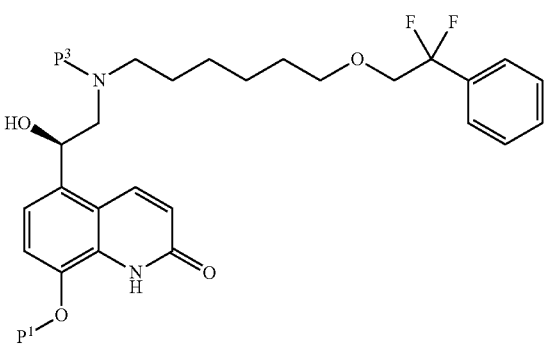

(Bp)

wherein $P^1$ and $P^3$ are as defined above;

a process for preparing a 5-(2-{[6-(2,2-difluoro-2-phenylethoxy)hexyl]amino}-1(R)-hydroxyethyl)-8-hydroxyquinolin-2(1H)-one compound of formula (I) or a pharmaceutically acceptable salt thereof,

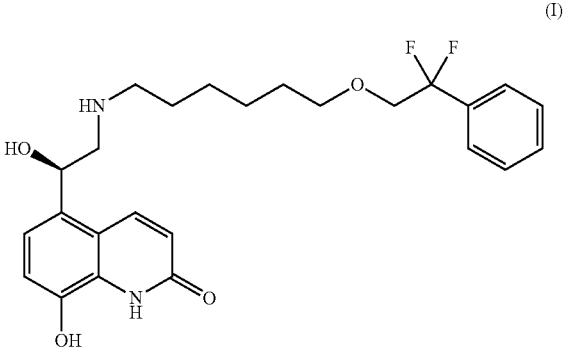 [SMILES: O=c1ccc2c([C@@H](O)CNCCCCCCOCC(F)(F)c3ccccc3)ccc(O)c2[nH]1]

(I)

which process comprises either b2) reduction of the aminoketone moiety of the compound of formula (A1) or a pharmaceutically acceptable salt thereof; or c1) removal of protecting groups $P^1$ and $P^3$ from the compound of formula (Bp) or a pharmaceutically acceptable salt thereof;

a process for preparing a compound of formula (A1) or a pharmaceutically acceptable salt thereof, which process comprises removal of protecting groups $P^1$ and $P^3$ from a compound of formula (Ap) or pharmaceutically acceptable salt thereof; and a process for preparing a compound of formula (Bp) or a pharmaceutically acceptable salt thereof, which process comprises reduction of the aminoketone moiety of a compound of formula (Ap) or a pharmaceutically acceptable salt thereof.

Contrary to the previous methods, the process of the invention as described above enables production of compound (I) and the pharmaceutically acceptable salts thereof in a very short way thus significantly reducing the reaction time. Moreover, compound (I) and its salts can easily be prepared from the novel intermediate (Ap) through only two synthetic steps while maintaining the yield and the purity of the final compound at acceptable levels.

Within the novel synthetic process of the present invention, the reduction of the amino ketone is preferably is carried out using a rhodium or ruthenium based catalyst a described below, so that the use of the borane dimethylsulfide complex is therefore avoided and thus all the drawbacks generated within the use of this reagent are now prevented. Moreover the use of the highly toxic hydrazine as a reagent is also avoided.

Contrary to the previous process, the reduction process of the aminoketone moiety is effected at a later stage. This fact allows the whole process to be carried out in a simple way and thus the whole process is more effective.

The term "pharmaceutically-acceptable salt" typically refers to a salt prepared from an acid which is acceptable for administration to a patient, such as a mammal. Such salts can be derived from from pharmaceutically-acceptable inorganic or organic acids.

Salts derived from pharmaceutically-acceptable acids include acetic, benzenesulfonic, benzoic, camphosulfonic, citric, ethanesulfonic, formic, fumaric, gluconic, glutamic, hydrobromic, hydrochloric, hydrofluoric, lactic, maleic, malic, mandelic, methanesulfonic, trifluoroacetic, mucic, nitric, pantothenic, phosphoric, succinic, sulfuric, tartaric, p-toluenesulfonic, xinafoic (1-hydroxy-2-naphthoic acid), napadisilic (1,5-naphthalenedisulfonic acid), triphenyl acetic and the like. Particularly preferred are salts derived from formic, fumaric, hydrobromic, hydrochloric, hydrofluoric, acetic, sulfuric, methanesulfonic, trifluoroacetic, xinafoic, tartaric, maleic, succinic and napadisilic acids.

Examples of particularly preferred pharmaceutically acceptable salts are selected from hydrochloride, napadisylate, sulfate, hydrogensulfate, methanesulfonate and trifluoroacetate, with hydrochloride, napadisylate and methanesulfonate more preferred, and napadisylate most preferred.

As skilled chemist will appreciate, conversion of the compound of formula (Ap) or pharmaceutically acceptable salt thereof into a compound of formula (I) or a pharmaceutically acceptable salt, may typically involve either (i) reducing the aminoketone group and then removing protecting groups $P^1$ and $P^3$, or (ii) removing protecting groups $P^1$ and $P^3$ and then reducing the aminoketone group.

Thus, in a typical embodiment the process for preparing a 5-(2-{[6-(2,2-difluoro-2-phenylethoxy)hexyl]amino}-1(R)-hydroxyethyl)-8-hydroxyquinolin-2(1H)-one compound of formula (I) or a pharmaceutically acceptable salt thereof comprises:

b1) reduction of the aminoketone moiety of the intermediate of formula (Ap) or a pharmaceutically acceptable salt thereof, to give an intermediate of formula (Bp) or a pharmaceutically acceptable salt thereof,

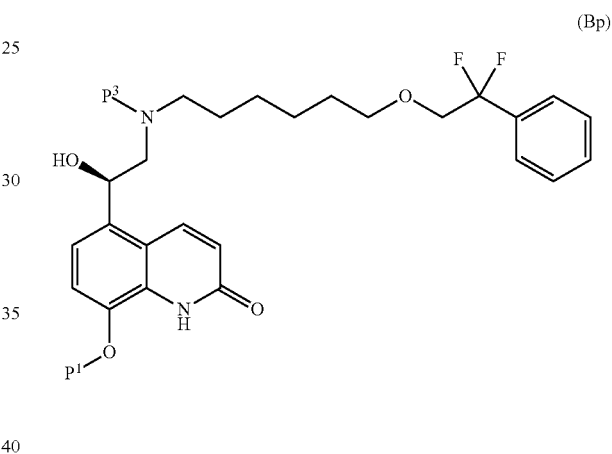

(Bp)

wherein $P^1$ and $P^3$ are as defined herein; and c1) removal of protecting groups $P^1$ and $P^3$ from the intermediate of formula (Bp) or a pharmaceutically acceptable salt thereof.

An example of such a process of the present invention can be summarised as depicted in Scheme 2.

Scheme 2

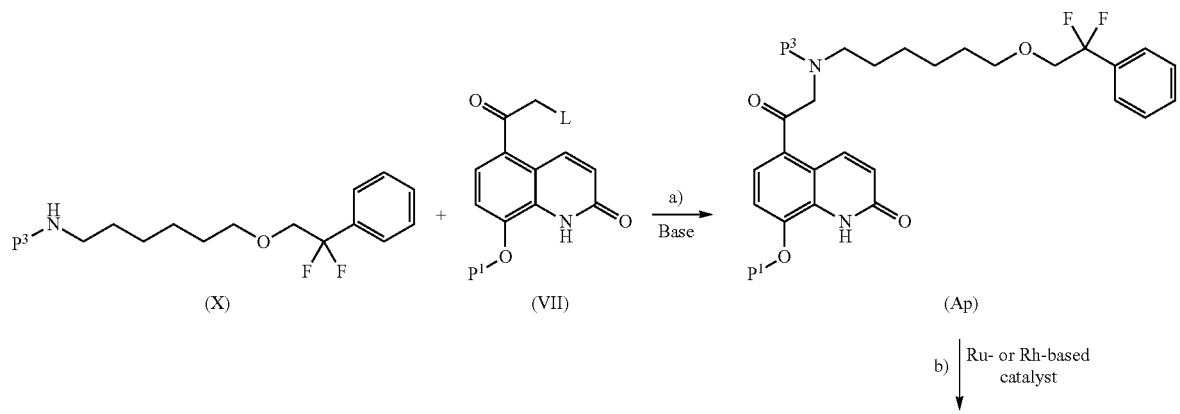

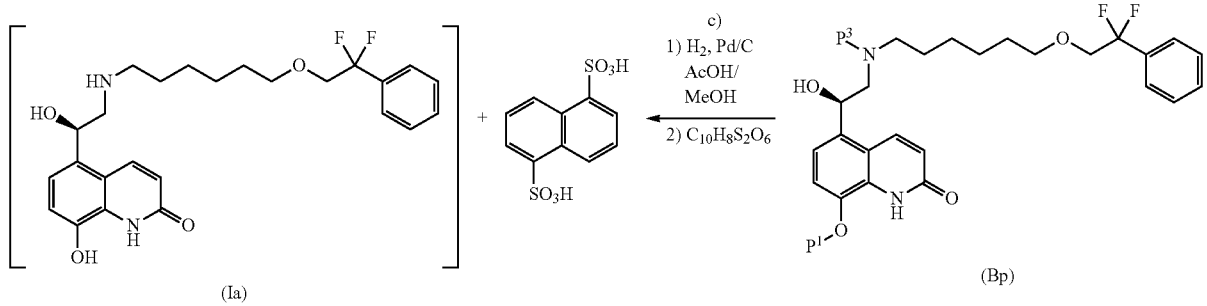

In an alternative typical embodiment, converting the process for preparing a 5-(2-{[6-(2,2-difluoro-2-phenylethoxy)hexyl]amino}-1 (R)-hydroxyethyl)-8-hydroxyquinolin-2(1H)-one compound of formula (I) or a pharmaceutically acceptable salt thereof comprises:

c2) removal of protecting groups $P^1$ and $P^3$ from the intermediate of formula (Ap) or a pharmaceutically acceptable salt thereof, to give an intermediate of formula (A1) or a pharmaceutically acceptable salt thereof:

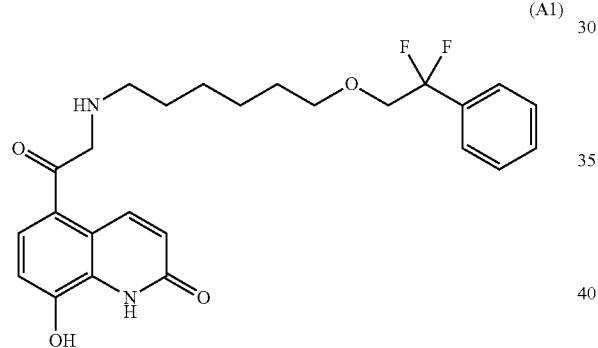

(A1)

and b2) reduction of the aminoketone moiety of the intermediate of formula (A1) or a pharmaceutically acceptable salt thereof.

An example of such a process of the present invention can be summarised as depicted in Scheme 3.

Scheme 3

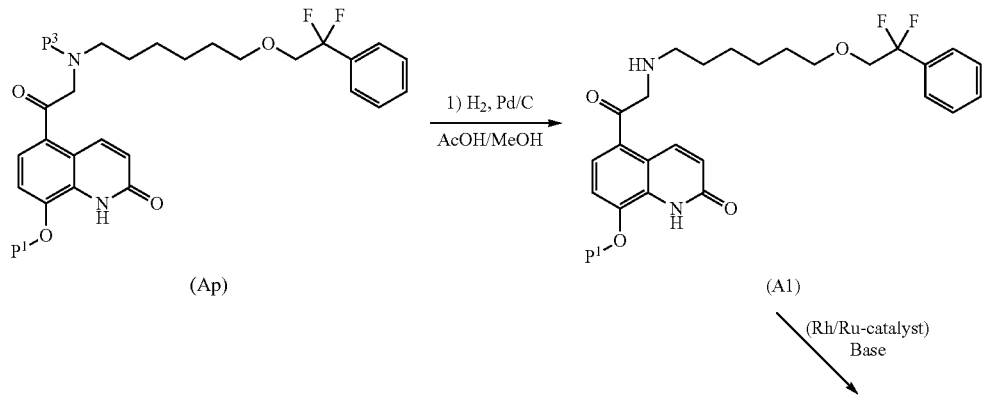

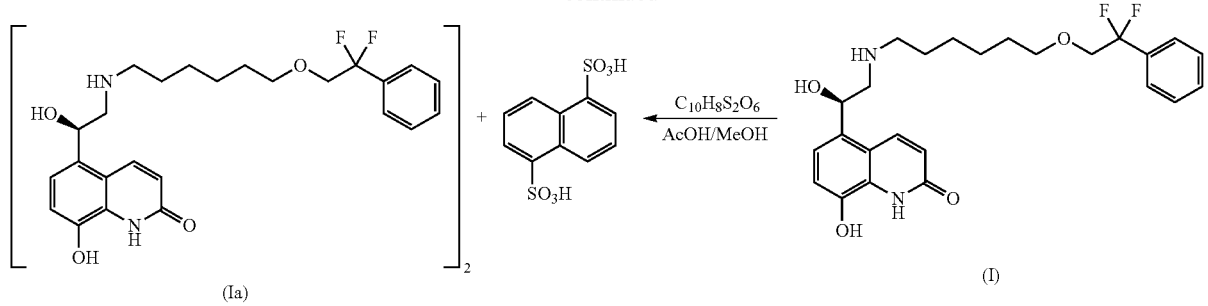

(Ia) → (I)

Preferably, the compound of formula (I) or a pharmaceutically acceptable salt thereof is prepared from the intermediate of formula (Ap) or pharmaceutically acceptable salt via intermediate (Bp).

Preferably, compounds of formula (Ap) are used in the form of a free base, rather than a pharmaceutically acceptable salt. Preferably, compounds of formula (A1) are used in the form of a free base, rather than a pharmaceutically acceptable salt. Preferably, compounds of formula (Bp) are used in the form of a free base, rather than a pharmaceutically acceptable salt. More preferably all of (Ap), (Bp) and (A1) are used in the form of a free base, rather than as pharmaceutically acceptable salts.

L is a leaving group. A skilled chemist would easily be able to select appropriate leaving groups for the L position. Examples of suitable leaving groups include halogen atoms, mesylate groups (—O—S(O)$_2$—CH$_3$) and triflate (—OS(O)$_2$—CF$_3$) groups.

Preferably, L is a halogen atom. More preferably, L is a bromine atom.

$P^1$ and $P^3$ are a hydroxy and an amino protecting group, respectively. A skilled chemist can easily select suitable protecting groups for the $P^1$ and $P^3$ positions. For example, appropriate protecting groups are discussed in T. W. Greene and G. M. Wuts, Protective Groups in Organic Synthesis, Third Edition, Wiley, New York, 1999, and references cited therein. Suitable deprotection method for such protecting groups are well known in the art, for example following the synthetic processes described in T. W. Greene and G. M. Wuts, Protective Groups in Organic Chemistry, Third Edition, Wiley, New York, 1999.

Examples of $P^1$ hydroxy-protecting groups include, but are not limited to, alkyl groups, such as methyl, ethyl and tert-butyl; acyl groups, for example alkanoyl groups, such as acetyl; arylmethyl groups, such as benzyl (Bn), p-methoxybenzyl (PMB), 9-fluorenylmethyl (Fm), and diphenylmethyl (benzhydryl, DPM); silyl groups, such as trimethylsilyl (TMS) and tert-butyldimethylsilyl (TBS); and the like. Preferably, $P^1$ is selected from a benzyl group and allyl group, more preferably a benzyl group.

Examples of $P^3$ amino-protecting groups include, but are not limited to, formyl; acyl, allyl groups, for example alkanoyl groups, such as acetyl; alkoxycarbonyl groups, such as tert-butoxycarbonyl (Boc); arylmethoxycarbonyl groups, such as benzyloxycarbonyl (Cbz) and 9-fluorenylmethoxycarbonyl (Fmoc); arylmethyl groups, such as benzyl (Bn), trityl (Tr), and 1,1-di-(4'-methoxyphenyl)methyl; silyl groups, such as trimethylsilyl (TMS) and tert-butyldimethylsilyl (TBS); and the like. Preferably, $P^3$ is a benzyl group, an allyl group or a tert-butyldimethylsilyl (TBS) group.

Preferably, $P^1$ and $P^3$ are the same or different and each represent a benzyl group or an allyl group, preferably a benzyl group. More preferably $P^1$ and $P^3$ represent the same protecting group.

Typically, the base used in step a) is selected from triethylamine, diisopropylethylamine or potassium carbonate, preferably triethylamine.

Typically, the aminoketone moiety is reduced in the presence of a rhodium or ruthenium-based catalyst.

Preferably, the aminoketone moiety is reduced using a ruthenium based catalyst. It has been found that within this type of catalysts very excellent results have been obtained with a very high conversion (>95%, ee>99%)

Examples of such catalysts are Noyori-type ruthenium catalysts such as, [(R)-Tol-Binap RuCl$_2$ (R)-DAIPEN], [(R)-Binap RuCl$_2$ (R)-DAIPEN], [(R)-Binap RuCl$_2$ (R,R)-DPEN]], [(R)-Binap RuCl$_2$ (S,S)-DPPN], [(R)-Tol-Binap RuCl$_2$ (R,R)-DPEN], [(R)-Xyl-PPhos RuCl$_2$ (S,S)-DPEN], [(R)-Xyl-PPhos RuCl$_2$ (S,S)-DPPN], [(S)-PPhos RuCl$_2$ (S)-DAIPEN], [(S)-PPhos RuCl$_2$ (S,S)-DPEN] and [(R)-PPhos RuCl$_2$ (R,R)-DCEN].

These catalysts are in the form of a ruthenium complex catalyst wherein RuCl$_2$ forms a complex compound with a diamine based chiral ligands from one side and with a diaryl-substituted phosphine derivative ligand on the other side. Examples of diamine-based chiral ligands are shown in the following Scheme 4.

Scheme 4

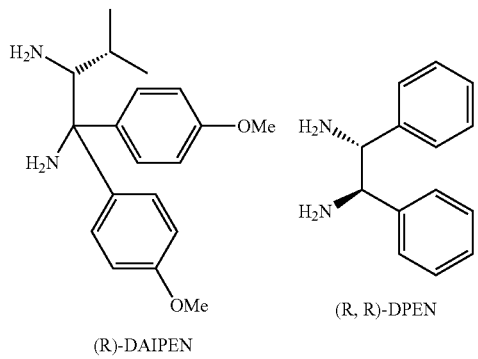

(R)-DAIPEN      (R, R)-DPEN

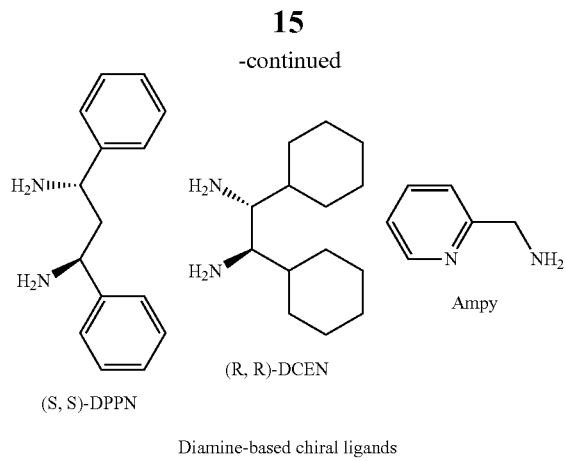

(S, S)-DPPN     (R, R)-DCEN     Ampy

Diamine-based chiral ligands

Examples of ligands based on diaryl-substitued phosphine are shown in the following Scheme 5.

Scheme 5

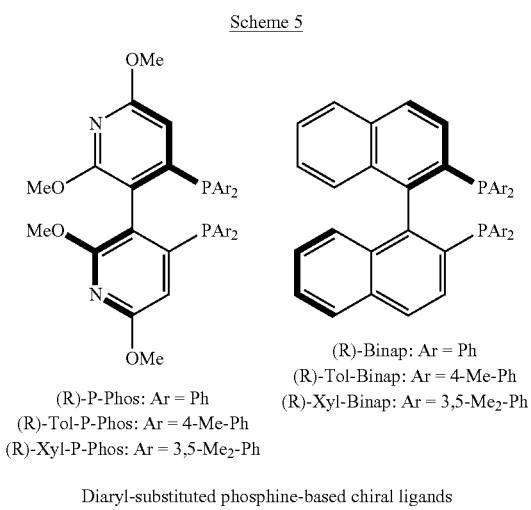

(R)-P-Phos: Ar = Ph
(R)-Tol-P-Phos: Ar = 4-Me-Ph
(R)-Xyl-P-Phos: Ar = 3,5-Me$_2$-Ph (R)-Binap: Ar = Ph
(R)-Tol-Binap: Ar = 4-Me-Ph
(R)-Xyl-Binap: Ar = 3,5-Me$_2$-Ph Diaryl-substituted phosphine-based chiral ligands Preferably, the Noyori-type ruthenium based catalyst are those complexes having PPhos, Binap or Tol-Binap as diaryl-substituted phosphine based chiral ligands and DAIPEN, DPEN or DCEN as diamine-based chiral ligands. More preferably, the Noyori-type ruthenium based catalysts are the ones depicted in the following scheme 6:

Scheme 6

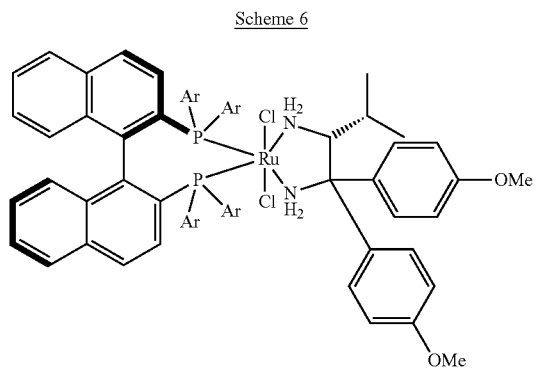

Ar = Tolyl: [(R)-Tol-Binap RuCl$_2$ (R)-DAIPEN]
Ar = Ph: [(R)-Binap RuCl$_2$ (R)-DAIPEN]

[(R)-PPhos Ru Cl$_2$ (R)-DAIPEN]

Typically, the aminoketone moiety is reduced in the presence of a rhodium or ruthenium-based catalyst at a temperature ranging from room temperature to 75° C., preferably at a temperature ranging from 65-70° C. Within this latter range and using the catalysts described above, a full conversion and higher enantiomeric excess values are obtained (99%, ee>99%).

Typically, the aminoketone moiety is reduced in the presence of a rhodium or ruthenium-based catalyst under a pressure ranging from 3 to 30 bar, preferably at a pressure of 20-28 bar, more preferably at a pressure of about 25 bar, most preferably at 25 bar.

Typically, the aminoketone moiety is reduced in the presence of a rhodium or ruthenium-based catalyst in the presence of a base. The base is preferably potassium tert-butoxide (tBuOK). Preferably the base is present in an amount between 1.5 and 3 equivalents of intermediate (Ap) or (A1).

Typically, the aminoketone moiety is reduced in the presence of a rhodium or ruthenium-based catalyst in the presence of an alcohol based solvent, such as methanol, ethanol, isopropanol, t-butanol or any mixture thereof. Preferably t-butanol and Isopropyl alcohol is used as a solvent.

Preferably, the aminoketone moiety is reduced in the presence of a rhodium or ruthenium-based catalyst, at a temperature ranging from room temperature to 75° C., more preferably 65-70° C., under a pressure ranging from 3 to 30 bar, more preferably 25 bar, and in the presence of a base.

As a skilled person will appreciate, the reaction conditions used in to remove protecting groups $P^1$ and $P^3$ will depend on the exact nature of protecting groups $P^1$ and $P^3$. A skilled person can readily determine suitable reaction conditions, for example by consulting the reference identified above. For example, if $P^1$ and $P^3$ represent benzyl, then typically these will be removed using Pd/C under hydrogen, preferably using a AcOH/MeOH solvent.

If an intermediate or compound is required in the form of a pharmaceutically acceptable salt, then this may be prepared by treating the intermediate or compound with the corresponding pharmaceutically acceptable acid.

Thus, pharmaceutically acceptable salts of compounds of formula (I) may be prepared by d) treating the compound of formula (I) with a pharmaceutically acceptable acid, to form the pharmaceutically acceptable salt.

Typically, the pharmaceutically acceptable acid used in step d) is selected from naphthalene 1,5-disulphonic acid and methane sulphonic acid. Preferably the pharmaceutically acceptable acid used in step d) is the naphthalene 1,5-disulphonic acid thus obtaining the napadisylate salt of formula (Ia):

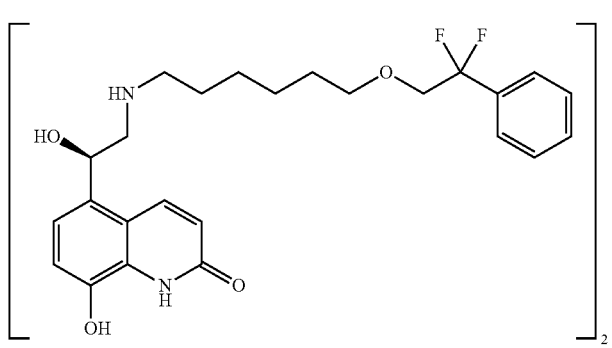

Alternatively, step d) may typically be omitted and compound (I) is obtained in a form of a free base.

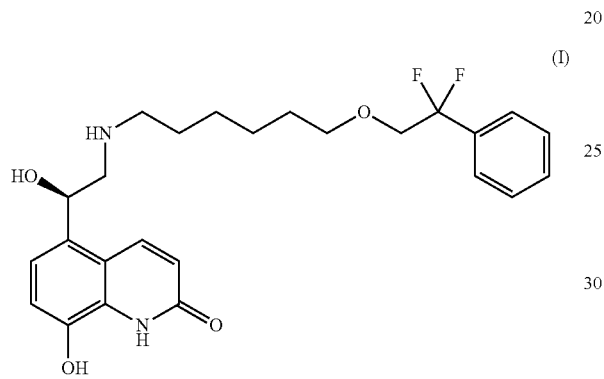

In the particular case wherein the pharmaceutically acceptable salt is napadisylate, this salt is typically the one described in WO 2008/095720. Preferably the napadisylate salt is a heminapadisylate salt or a mononapadisylate salt. A mononapadisylate salt typically contains between about 0.8 and 1.2 molar equivalents of naphthalene-1,5-disulfonic acid per molar equivalent of the free base, more typically about 1.0 molar equivalents of naphthalene-1,5-disulfonic acid per molar equivalent of the free base. A heminapadisylate salt typically contains between about 0.35 and 0.65 molar equivalents of naphthalene-1,5-disulfonic acid per molar equivalent of the free base, more typically about 0.5 molar equivalents of napthalene-1,5-disulfonic acid per molar equivalent of the free base as disclosed in formula (Ia)

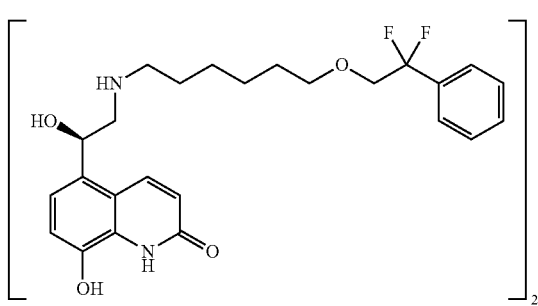

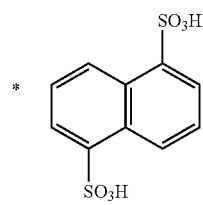

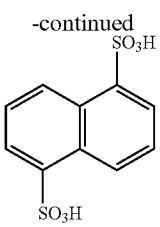

In one aspect of the present invention, compounds of formula (Ap) may be prepared in a form of any pharmaceutically acceptable salt thereof such as hydrochloride, napadisylate, sulfate, hydrogensulfate, methanesulfonate and trifluoroacetate.

In another aspect of the present invention, the reduction process of step b1) may be carried out using the intermediate (Ap) in its pharmaceutically acceptable salt form, such as for example, a napadisylate or a hydrochloride. In this case the reduced compound (Bp) is obtained in a free base form.

The starting compound of formula (X) may be obtained by addition of the corresponding amine to the bromated derivative of formula (IX) in the presence of a base such as triethylamine as depicted in Scheme 7. The reaction is carried out under inert atmosphere at a temperature ranging from 40-50° C.

Scheme 7

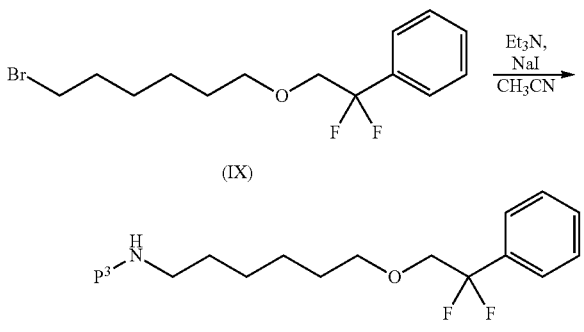

Alternatively, Intermediate of formula (X) can also be obtained according to the following scheme 8.

Scheme 8

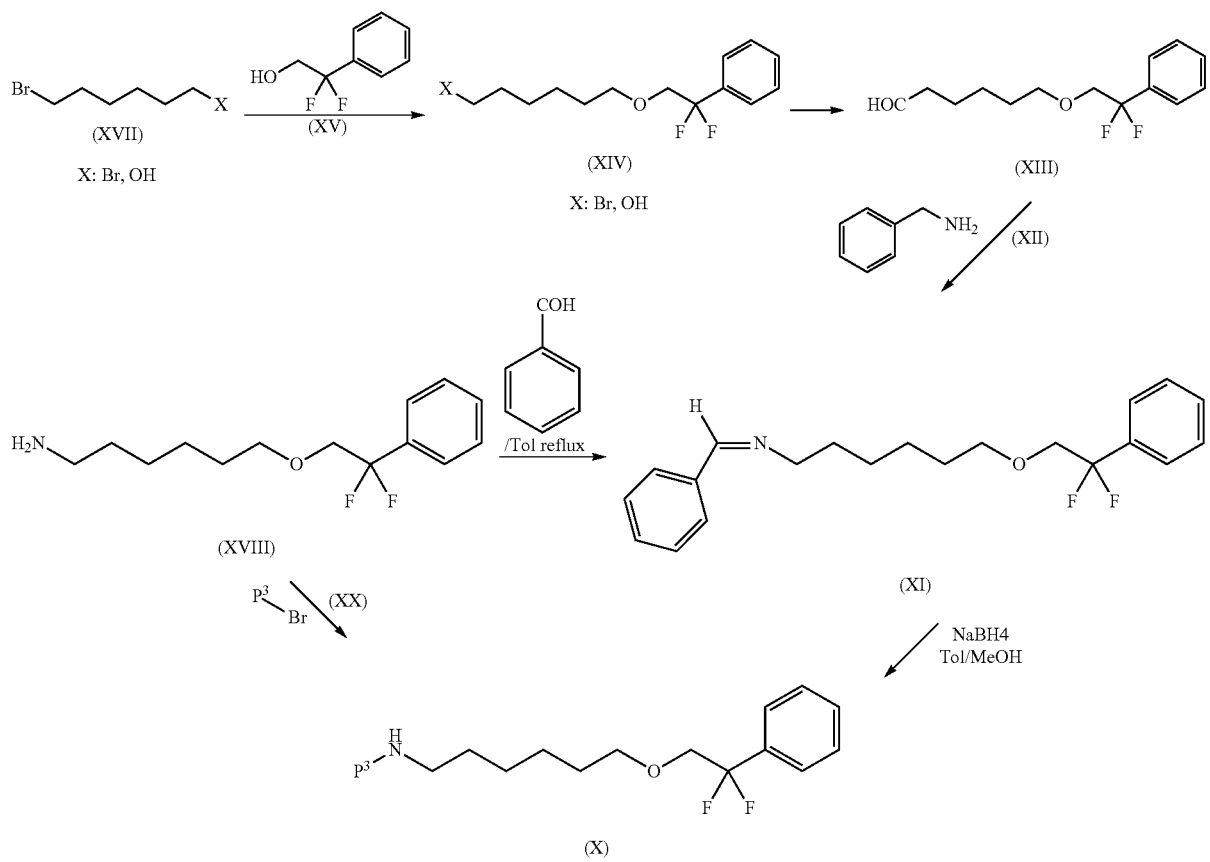

Intermediate of formula (X) may be obtained from intermediate (XI) in the presence of Sodium Borohydride in a mixture of Toluene-Methanol. Intermediate of formula (XI) may be similarly obtained by reaction of benzylamine of formula (XII) with the aldehyde derivative of formula (XIII). Alternatively, intermediates of formula (XI) may also be obtained by reacting the amine derivative of formula (XVIII) with benzaldehyde of formula (XIX) in the presence in a suitable solvent such as toluene at a temperature ranging from 100° C. to reflux.

Intermediate of formula (XIII) may be obtained by reacting the bromo derivative of formula (XVII) with intermediates of formula (XV) in the presence of a base as NaOH, yielding intermediates (XIV) which in turn may be transformed into intermediates of formula (XIII).

Alternatively, the protected amine derivative of formula (X) may be obtained by reaction of the corresponding amine of formula (XVIII) with a suitable protective group of formula (XX) following a synthetic procedure already known in the art.

Intermediates of formula (X) may optionally be obtained in a form of a pharmaceutically acceptable salt thereof, preferably hydrochloride salt. In this case, this salt may be prepared by treating a solution of intermediates of formula (X) with concentrated HCl following conventional synthetic methods already known in the art.

The reagents and solvents used in the present invention are commercially available, for example from Aldrich Chemical Company, Inc. or Fluka Chemie GmbH.

The method of synthesis described in the present invention will be further illustrated by the following examples. The examples are given by the way of illustration only and are not to be construed as limiting.

The structures of the prepared compounds were confirmed by $^1$H-NMR and MS. NMR were recorded using a Varian Gemini-200 NMR spectrometer operating at frequency of 200 or 300 MHz. Tetramethyl silane was used as a reference and samples were solved in deuterated dimethylsulphoxide (DMSO-$d_6$) or deuterated chloroform (CDC$_3$).

Their purity was determined by HPLC, in Alliance 2795 Waters instrument equipped with diode array detector (DAD) and ZMD or ZQ mass detector (electrospray ionization). HPLC method used a Symmetry C18 column (3.5 μm, 21×100 mm) and mobile phase was composed by two phases: Phase A: Buffered (Formic acid/ammonia) aqueous solution at pH: 3. Phase B: 50.50 mixture acetonitrile/methanol with ammonia formiate. Gradient was from 0% to 95% of phase B in 10 minutes.

Preparative HPLC-MS experiments were performed on a Gilson instrument equipped with a binary pump (Gilson piston pump 321); a vacuum degasser (Gilson 864); an injector-fraction collector (Gilson liquid handler 215); two injection modules, analytical and preparative (Gilson 819); a valve (Gilson Valvemate 7000); a ¹/₁₀₀₀ splitter (Acurate by LC Packings); a make-up pump (Gilson 307); a diode array detector (Gilson 170) and a MS detector (a Thermoquest Finnigan aQa, a quadrupole mass spectrometer with ES and APCI ionisation modes). The HPLC-MS instrument was controlled by an IBM PC.

EXPERIMENTAL SECTION

Intermediate (Xa). N-Benzyl-6-(2,2-difluorophenylethoxy)hexane-1-amine

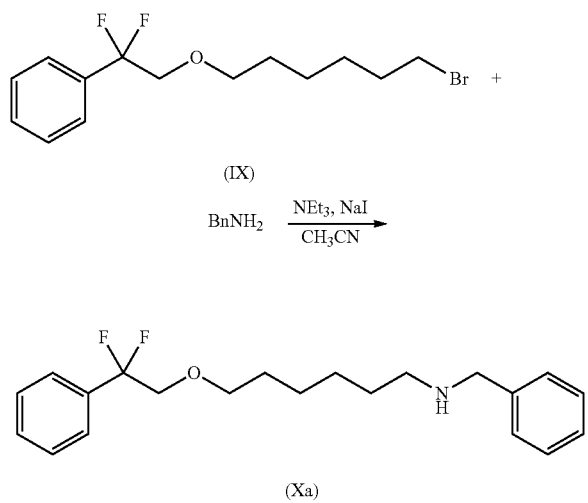

To a solution of 13.8 ml (0.126 mol) of benzylamine in 60 ml of acetonitrile were added 11.7 ml of triethylamine and 0.64 g (4.2 mmol) of NaI. The reaction mixture was heated at 40° C. To this solution, the difluorobenzyl bromated derivative of formula (IX) (14.49 g, 0.042 mol) was added dropwise followed by 10 ml of acetonitrile.

The reaction mixture was stirred for 5 hours at 45° C. under Nitrogen atmosphere. Once finished, the solvent was removed and the oily residue was treated with dichloromethane (70 ml) and water (70 ml). The aqueous phase was extracted with dichloromethane (70 ml). Finally the organic extracts were dried with MgSO$_4$ and the solvent removed under reduced pressure. The crude thus obtained was dissolved in 5 volumes of CH$_2$Cl$_2$ (106 ml), then 3 equivalents of hydrochloride acid (6M solution, 31 ml) were added. The mixture was stirred at room temperature during 15 minutes. The 15 organic layer was washed twice with water (50 ml×2) and dried with MgSO$_4$. The solvent was removed under reduced pressure giving the title product in a form of hydrochloride salt as white foam. The product obtained was additionally treated with 4 volumes of diethyl ether (Et$_2$O) and stirred at room temperature for at least 1 hour. The resulting solid is filtered and dried under vacuum (14.466 g of the hydrochloride salt are obtained).

This salt is solved again in CH$_2$Cl$_2$ (72 ml) and treated with a saturated aqueous solution of Sodium Bicarbonate (115 ml). After stirring at room temperature during 45 minutes, the layers are separated and the organic one is washed with water (36 ml), dried over MgSO$_4$ and the final solution evaporated to dryness. The title intermediate is obtained as a free base (12.681 g; yield: 81%).

Step a)

a.1) 5-(2-(benzyl(6-(2,2-difluoro-2-phenylethoxy)hexyl)amino)acetyl)-8-(benzyloxy)-quinolin-2(1H)-one (Ap1). (wherein both P$^1$ and P$^3$ represent a benzyl group)

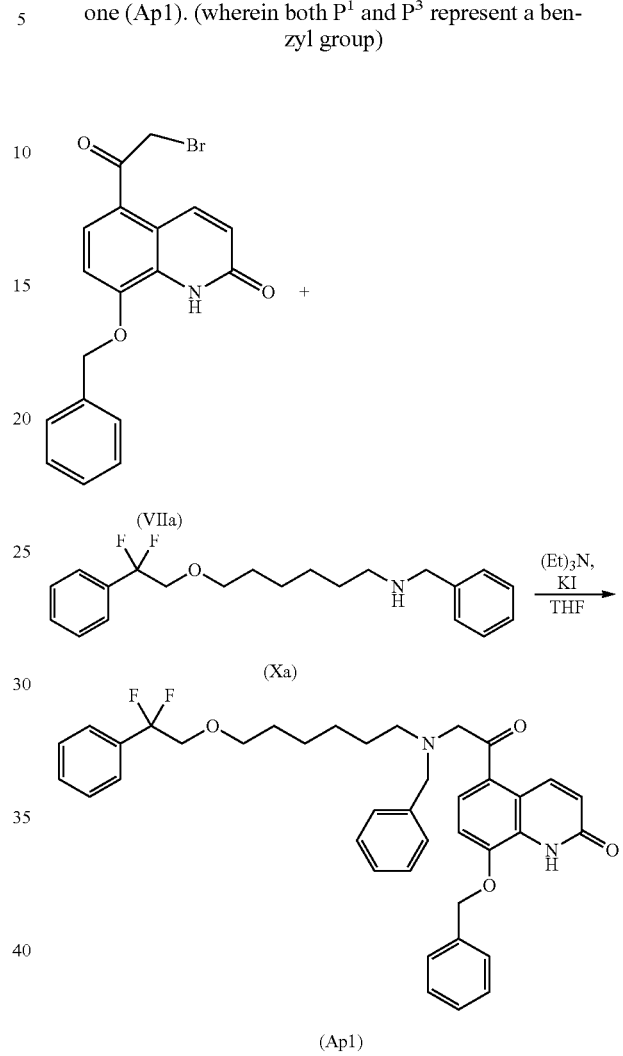

To a solution of 8-(benzyloxy)-5-(2-bromoacetyl)quinolin-2-2(1H)-one) (VIIa) in THF (47.89 g, 200 ml) were added 20.6 ml of triethylamine and 2.14 g of KI. Then, 44.7 g of N-Benzyl-6-(2,2-difluorophenylethoxy)hexane-1-amine (Xa) in 100 ml of THF were added dropwise to the previous mixture during about 5 minutes. The reaction system was purged and heated to 60° C. under argon atmosphere. Once the reaction was completed (2 h approx.), the solvent was concentrated under vacuum and the resulting crude treated with 320 ml of Ethyl acetate and 320 ml of water. The organic layer was washed with 320 ml of saturated solution of NaCl, dried with MgSO$_4$ and solvent removed under reduced pressure. 82.2 g of crude (Ap1) free base in a form of an oily residue is obtained (purity by HPLC: 85% approx).

Purification Process of Ap1

This oily residue can be purified by column chromatography, or by means of an appropriate salt crystallization.

When the crude product is purified by column chromatography, Ap1 is obtained, with a purity of 97-98% by HPLC. The global yield (reaction+purification) is around 70%.

In case of purification by recrystallization, the process may be carried out as follows:

Napadisylate of 5-(2-(benzyl(6-(2,2-difluoro-2-phenylethoxy)hexyl)amino)acetyl)-8-(benzyloxy)-quinolin-2(1H)-one (Ap1 Napadisylate)

82.2 g of crude (Ap1) are dissolved in Methanol (822 ml) and the Naphthalene-1,5-disulfonic acid tetrahydrate (23.19 g) is added, and the solution heated at reflux. The solvent is removed, giving rise to 98.2 g of the salt. This product is maintained at 55-60° C. during about 2 h in a mixture of terc-butylmethyleter (786 ml) and Methanol (491 ml). The mixture is cooled to 0° C., filtered and the solid obtained is washed with more solvent (TBME/MeOH (1.6:1)). After drying, 73.2 g of product are obtained (HPLC purity: 98.2%). The global yield, including preparation of crude (Ap1), and crystallization of the napadisylate, is 72%.

Once purified as the napadisylate, intermediate Ap1 can be obtained as a free base with the following method:

Ap1 Napadisylate (73.2 g) is charged in a reactor with $CH_2Cl_2$ (740 ml) and stirred at room temperature with an aqueous 1 M solution of NaOH (470 ml). After dissolution of the product the layers are separated. The organic layer is washed again with more water (750 ml). After removing the solvent from the organic extract, Ap1 is obtained as a residue in an almost quantitative way (yield 100% approx.).

Hidrochloride of 5-(2-(benzyl(6-(2,2-difluoro-2-phenylethoxy)hexyl)amino)acetyl)-8-(benzyloxy)-quinolin-2(1H)-one (Ap1 HCl)

60.2 g of product (Ap1) is dissolved in 740 ml of $CH_2Cl_2$. Then, to the resulting solution, 8.4 ml of concentrated HCl 37% are added. The solvent is removed under reduced pressure giving the corresponding (Ap1) HCl as a white foam.

Step a)

a.2.) 5-(2-(allyl(6-(2,2-difluoro-2-phenylethoxy)hexyl)amino)acetyl)-8-(benzyloxy)-quinolin-2(1H)-one. (Ap2) ($P^1$ represents a benzyl group while $P^3$ represents an allyl group)

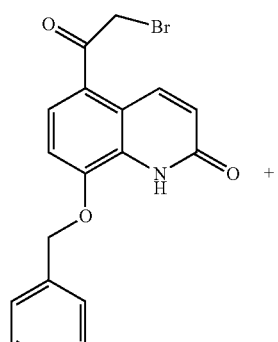

(VIIa)

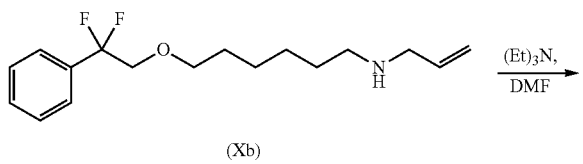

(Xb)

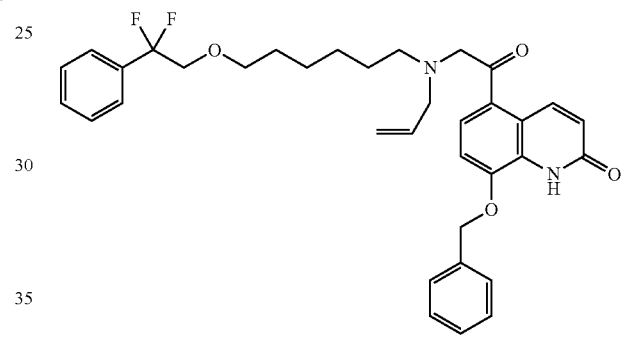

(Ap2)

To a solution of 8-(benzyloxy)-5-(2-bromoacetyl)quinolin-2-2(1H)-one) (VIIa) in DMF (7.46 g, 12 ml) was added 3.3 ml of triethylamine. Then, 8.938 g of N-Allyl-6-(2,2-difluorophenylethoxy)hexane-1-amine (Xb) in 8 ml of DMF were added dropwise to the previous mixture. The reaction system was purged and heated to 60° C. under Nitrogen atmosphere. Once the reaction was completed (3 h approx.), the reaction mixture is treated with 33 ml of Ethyl acetate and 33 ml of water. The organic layer was washed with a saturated solution of NaCl, dried with $Na_2SO_4$ and solvent removed under reduced pressure. 14.677 g of crude (Ap2) free base in a form of an oily residue are obtained.

This oily residue is purified by flash chromatography. Ap2 is obtained, with a purity of 94.4% by HPLC. The global yield (reaction+purification) is 63%.

Step b) (R)-5-(2-(benzyl(6-(2,2-difluoro-2-phenylethoxy)hexyl)amino)-1-hydroxyethyl)-8-(benzyloxy)quinolin-2(1H)-one. (Bp1)

Example 1

Step b) Using Ap1 (Base) as a Reagent

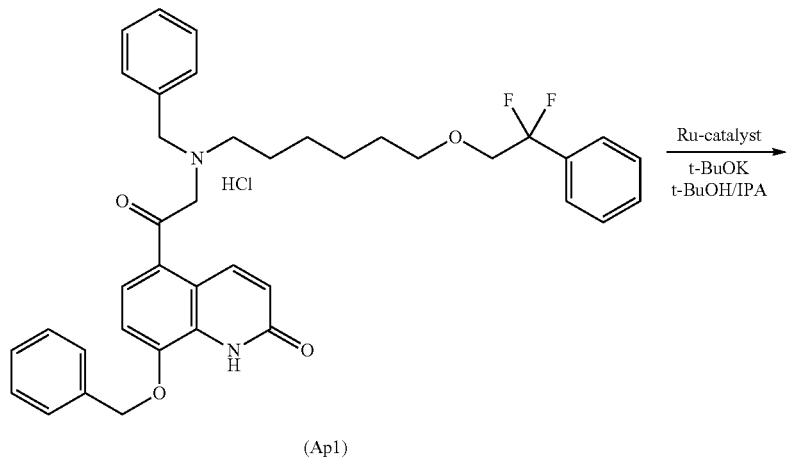

In a 1000 ml stainless steel reactor equipped with overhead stirring were charged 115 mg of (R)-tol-BINAP RuCl₂ DAIPEN. 57.96 g (Ap1) were dissolved in 341 ml of isopropanol by gently warming. The warm solution was charged to the reactor. The reactor was sealed and purged three times with $N_2$. The reactor was then purged five times with $N_2$ while stirring. The reactor was then charged with 137 ml of 1M t-BuOK in t-Butanol. The reactor was again purged three times with $N_2$ without stirring and then purged five times with $N_2$ while stirring. The reactor was then purged with $H_2$ five times while stirring and pressurized to 4 bars. The reactor was heated to 65° C. (internal temperature). After the temperature was reached, the reactor was further pressurized to 25 bars and allowed to stir for 12 hours while the hydrogen consumption was monitored. After 12 hours the reactor was cooled, vented and purged with $N_2$. The reactor was then opened and the mixture was filtered on 200 g Silica using an additional 1 l of isopropanol as a rinse. The reaction mixture was then concentrated on a rotary evaporator to give a brown oil of (R)-8-(benzyloxy)-5-(2-((tert-butyldimethyl-silyl)(6-(2,2-difluoro-2-phenylethoxy)hexyl)amino)-1-hydroxyethyl) quinolin-2(1H)-one (Bp1) (56 g, 97% yield). The samples were analyzed by HPLC. (Total impurities by HPLC: 6%; e.e.: 99%)

Example 2

Step b) Using Ap1 HCl as a Reagent

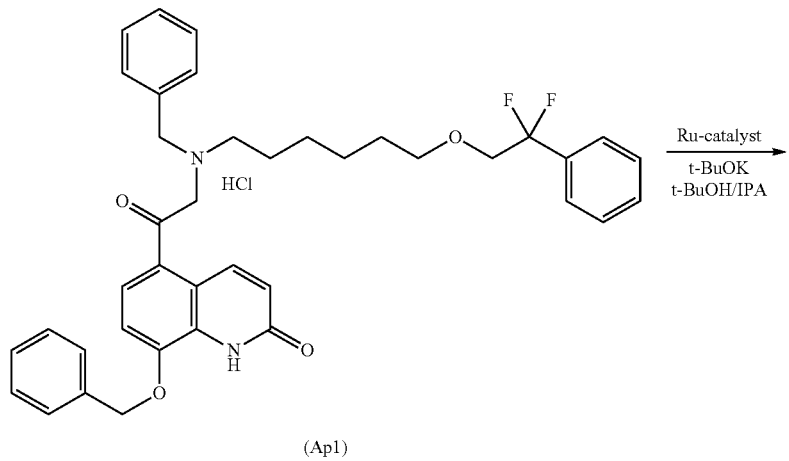

(Ap1)

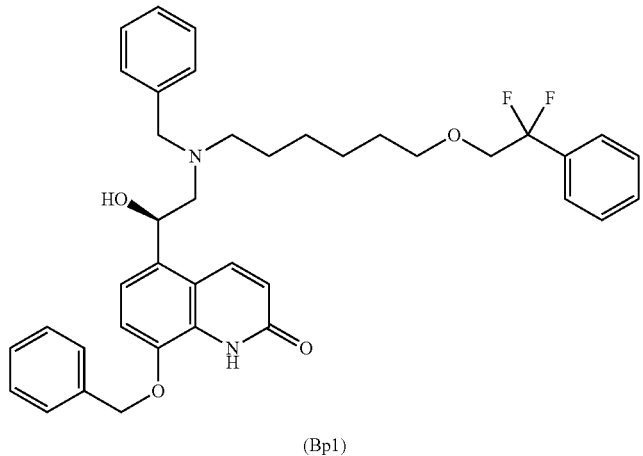

(Bp1)

In a 1000 ml stainless steel reactor, equipped with overhead stirring, was charged 84.7 mg of (R)-tol-BINAP RuCl$_2$ DAIPEN, 49.1 g (Ap1 HCl) and 304 ml of isopropanol. The reactor was sealed and purged three times with N$_2$. The reactor was then purged five times with N$_2$ while stirring. The reactor was then charged with 183 ml of 1M t-BuOK in t-Butanol. The reactor was again purged three times with N$_2$ without stirring and then purged five times with N$_2$ while stirring. The reactor was then purged with H$_2$ five times while stirring and pressurized to 4 bars. The reactor was heated to 65° C. (internal temperature). After the temperature was reached, the reactor was further pressurized to 25 bars and the hydrogen consumption was monitored. Once completed the reactor was cooled, vented and purged with N$_2$. The reactor was then opened and the mixture was filtered on 160 g Silica using an additional 1 L of isopropanol as a rinse. The reaction mixture was then concentrated on a rotary evaporator to give a brown oil of (R)-8-(benzyloxy)-5-(2-((tert-butyldimethylsilyl) (6-(2,2-difluoro-2-phenylethoxy)hexyl)-amino)-1-hydroxyethyl)quinolin-2(1H)-one (Bp1) (45.45 g, 97% yield). The samples were analyzed by HPLC. (Total impurities by HPLC: 9%; e.e.: 97%).

Example 3

Step b) Using Napadisylate Salt of (Ap1) as a Reagent

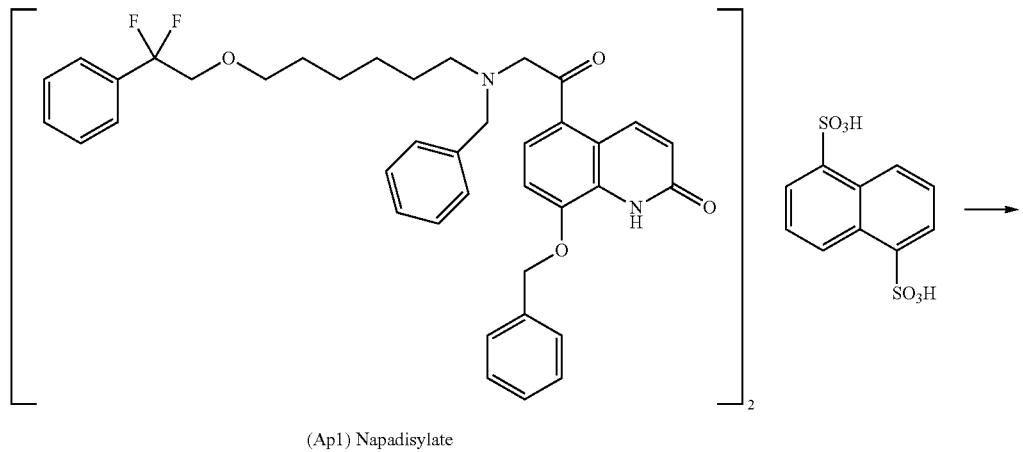

(Ap1) Napadisylate

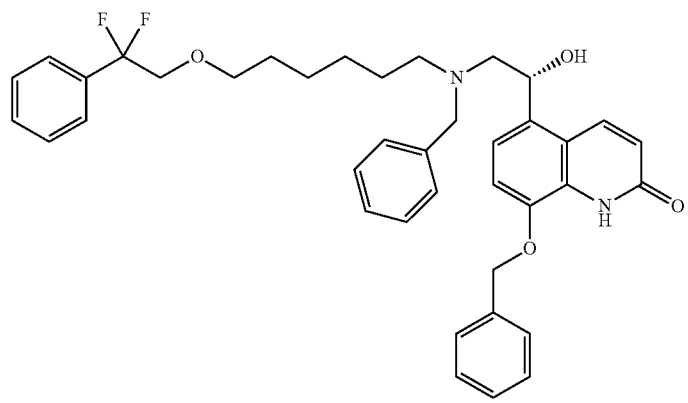

Bp1

In a reactor equipped with overhead stirring was charged 8 mg (R)-tol-BINAP RuCl₂ DAIPEN, 6.1 g of Ap1 napadisylate and 25 mL of isopropanol The reactor was purged with nitrogen 5 times without stirring and 5 times with stirring. 28 mL of 1 M t-BuOK in t-BuOH was added. The reactor was again purged with nitrogen five times without stirring and five times while stirring. The reactor was then pressurized to 4 bar hydrogen and heated to 65° C. (internal temperature). After the temperature was reached, the reactor was further pressurized to 25 bar hydrogen and allowed to stir for 23 hours while the hydrogen consumption was monitored. After 23 hours the reactor was cooled, vented and purged with N₂. The solution was filtrated and concentrated on a rotary evaporator to give a brown oil (3.65 g, 73% yield).

Step b) (R)-5-(2-(allyl(6-(2,2-difluoro-2-phenylethoxy)hexyl)amino)-1-hydroxyethyl)-8-(benzyloxy)quinolin-2(1H)-one. (Bp2)

Step b) Using Ap2 HCl as a Reagent

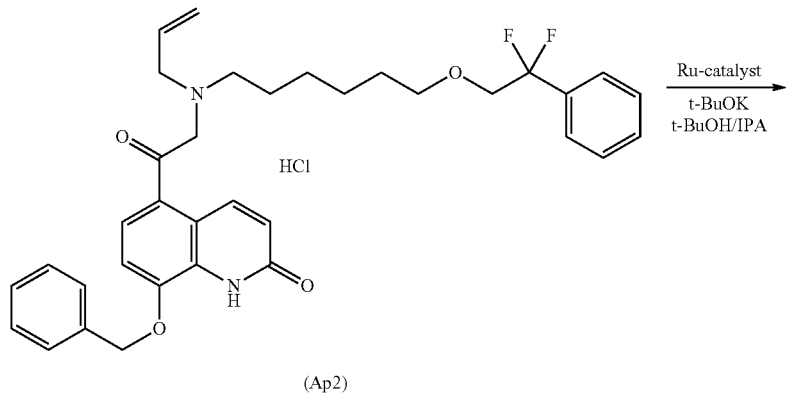

(Ap2)

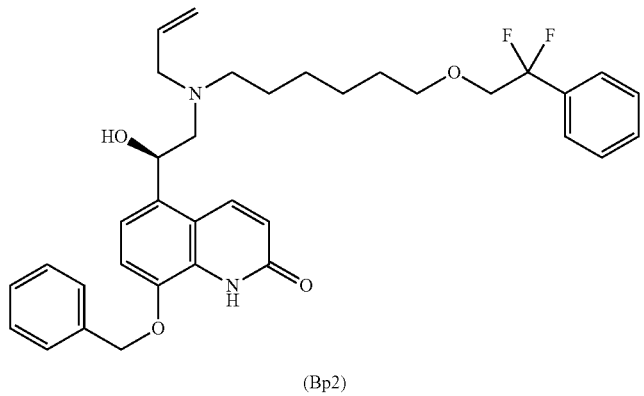

(Bp2)

In a 50 ml Parr autoclave are charged 8.6 mg of (R)-tol-BINAP RuCl$_2$ DAIPEN, 470 mg Ap2.HCl and 5 ml Isopropanol. The autoclave is closed and inerted with Nitrogen. Then 1.61 ml of t-BuOK 1M in t-BuOH are added and the mixture purged several times with Hydrogen. The mixture is heated to 45° C. and pressurized with Hydrogen to 25 bar, maintaining these conditions during 16 hours. After standard work-up, the crude product is isolated and analyzed (HPLC purity 94%; e.e.: 95.5%).

Step c)

5-((1R)-2-{[6-(2,2-difluoro-2-phenylethoxy)hexyl]amino}-1-hydroxyethyl)-8-hydroxyquinolin-2(1H)-one, napadisylate salt (compound Ia)

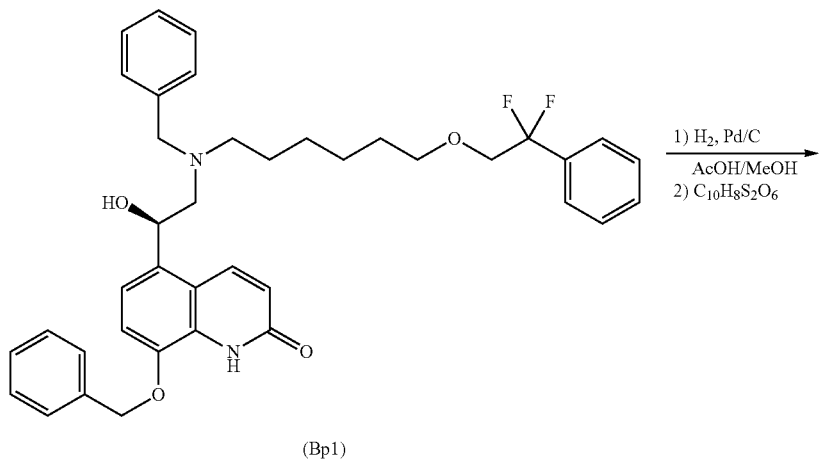

(Bp1)

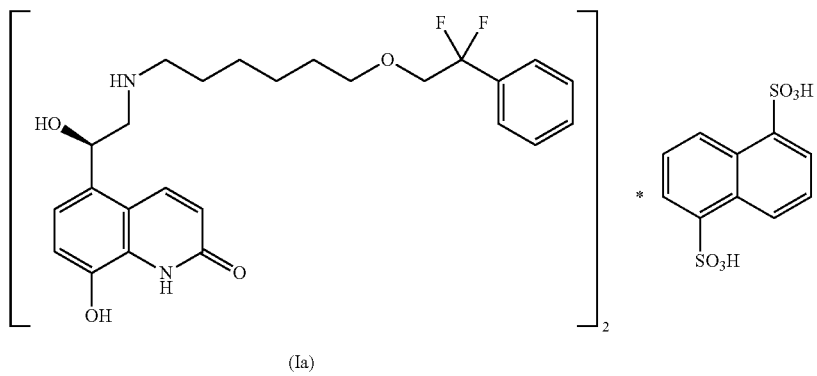

(Ia)

Intermediate of formula (Bp1) (30.1 g) was dissolved in 150 ml of Methanol and 150 ml of Acetic Acid, and 4.80 g of Pd/C 10%, 50% water were added. After several purges of nitrogen, the reaction mixture was hydrogenated at atmospheric pressure and a temperature of 20-30° C. during 8 hours. The catalyst was then filtered and washed with 120 ml of methanol. After that, more methanol (30 ml) and Acetic Acid (150 ml) were added to the liquid filtrate.

A solution of 12.0 g of 1,5-naphthalenedisulfonic acid tetrahydrate in 30 ml of Methanol and 30 ml of Acetic Acid was added to the previous solution. The mixture was heated to reflux during 30 minutes and cooled to room temperature. The solid was filtered and washed with methanol. Finally, the wet cake was suspended again in methanol (870 ml) and heated to reflux during 30 minutes and cooled to room temperature. The obtained solid was filtered and washed with methanol. After drying the product at 50° C. under vacuum, 18.8 g of compound (Ia) are obtained (yield 66.3%).

The analysis of this product shows a level of HPLC impurities of 1.03% and 0.6% of S enantiomer.

the overall yield of 5-((1R)-2-{[6-(2,2-difluoro-2-phenylethoxy)hexyl]amino}-1-hydroxyethyl)-8-hydroxyquinolin-2(1H)-one napadisylate salt (Ia) is calculated to be about 50%, being the product obtained of the adecuate purity (HPLC imp=1.03%, e.e. >99%).

From intermediate VIIa, the overall yield of 5-((1R)-2-{[6-(2,2-difluoro-2-phenylethoxy)hexyl]amino}-1-hydroxyethyl)-8-hydroxyquinolin-2(1H)-one napadisylate salt (Ia) is calculated to be about 50% being the product obtained of the adecuate purity (HPLC imp=1.03%, e.e. >99%).

The following example describes the synthetic process for preparing intermediate A1 (wherein both $P^1$ and $P^3$ are a hydrogen atom)

5-(2-(6-(2,2-Difluoro-2-phenylethoxy)hexylamino) acetyl)-8-(hydroxyquinolin-2(1H)-one Hydrochloride. (A1 HCl)

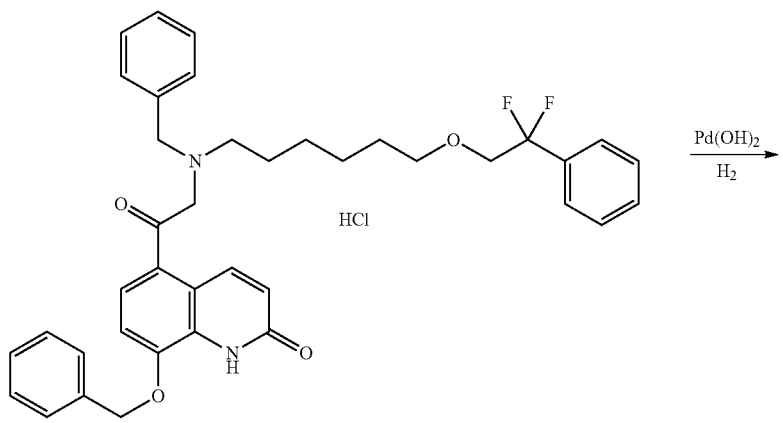

(Ap1)

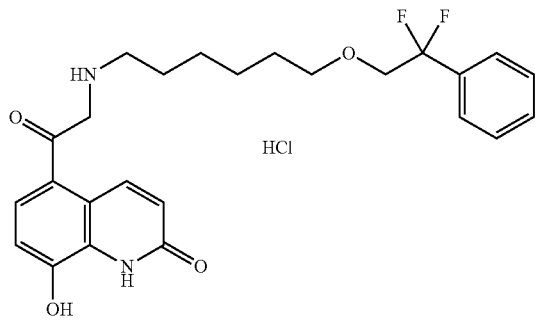

(A1)

In a 1000 ml stainless steel reactor equipped with overhead stirring are charged 17.978 g of Ap1.HCl and 180 ml of Methanol. Under Argon atmosphere, 1.79 g of Palladium Hydroxide are charged. After purging several times with Hydrogen, the reaction mixture is maintained stirring at room temperature under a Hydrogen atmosphere. Once the reaction is completed (approx. 40 minutes), Hydrogen is purged with Argon and the catalyst removed by filtration. After evaporating the solvent, the residue is solved in a hot mixture of 150 ml of Acetonitrile and 50 ml of Methanol. When cooling to 0° C., A1 HCl crystallizes. The solid is filtered, washed and dried, yielding 6.29 g (purity HPLC: 99.2%).

TABLE 1 comparative results

| Steps | According to WO 2006/122788 | According to WO 2010/102831 | According to the present invention |
|---|---|---|---|
| VIIa to Ia | 6-8% | 45% | 46% |
| Impurities of final product (Ia) | 5.8% | 1.5% | 1.0% |

As it can be observed from the table, the new process according to the present invention allows obtaining compound (Ia) within similar yields using only 3 reaction steps when compared with the previous processes described in the art. In addition, the impurity level of compound (Ia) is lower than the product obtained with previous procedures. This is achieved by using a new intermediate compound (Ap) thus simplifying the reaction steps and avoiding the use and handling of other substances which are known to be very toxic and highly potent.

The invention claimed is:

1. A process for preparing 5-(2-{[6-(2,2-difluoro-2-phenylethoxy) hexyl]amino}-1(R)-hydroxyethyl)-8-hydroxyquinolin-2(1H)-one or a pharmaceutically acceptable salt thereof, comprising:
   reducing and deprotecting a compound of formula (Ap) or a pharmaceutically acceptable salt thereof,

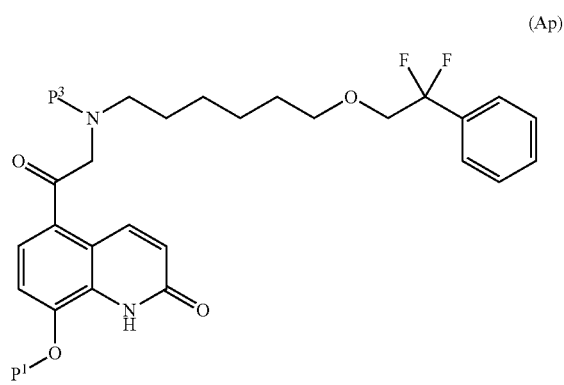

(Ap)

wherein $P^1$ represents a hydroxy protecting group and $P^3$ represents an amino protecting group, and wherein the aminoketone moiety is reduced in the presence of a rhodium or ruthenium-based catalyst.

2. The process according claim 1, comprising:
   reduction of the aminoketone moiety of the compound of formula (Ap) to give a compound of formula (Bp) or a pharmaceutically acceptable salt thereof,

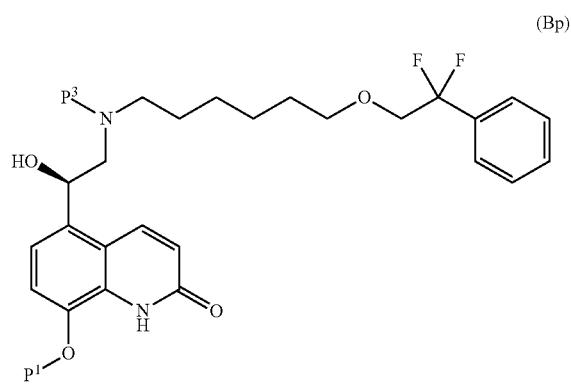

(Bp)

and
removal of protecting groups $P^1$ and $P^3$.

3. The process according to claim 1, comprising:
   removal of the protecting groups $P^1$ and $P^3$ from the compound of formula (Ap) to give a compound of formula (A1) or a pharmaceutically acceptable salt thereof:

(A1)

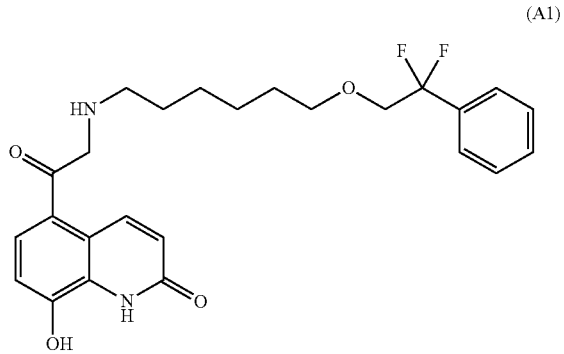 [SMILES: O=C(CNCCCCCCOCC(F)(F)c1ccccc1)c1ccc(O)c2[nH]c(=O)ccc12]

and
reduction of the aminoketone moiety of the compound of formula (A1).

4. A process for preparing 5-(2-{[6-(2,2-difluoro-2-phenylethoxy)hexyl]amino}-1(R)-hydroxyethyl)-8-hydroxyquinolin-2(1H) one or a pharmaceutically acceptable salt thereof, comprising:
  removal of protecting groups P¹ and P³ from the compound of formula (Ap) or a pharmaceutically acceptable salt thereof, (Ap)

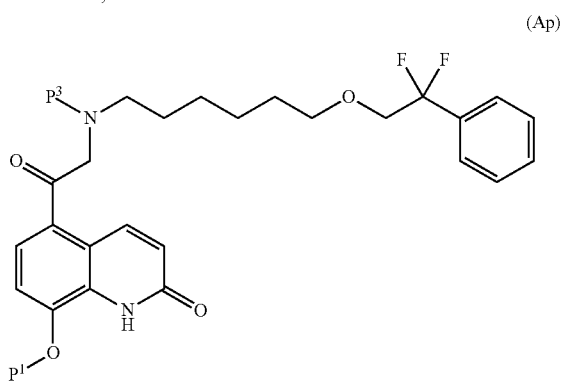

wherein P¹ represents a hydroxy protecting group and P³ represents an amino protecting group, to give a compound of formula (A1) or a pharmaceutically acceptable salt thereof:

(A1)

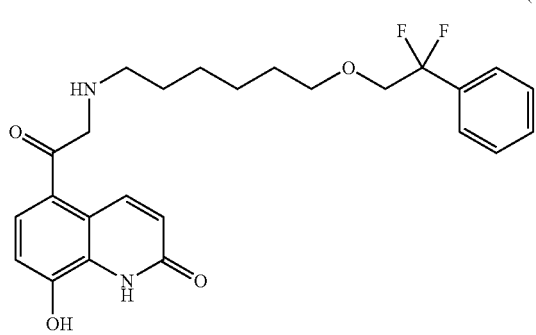

and
reduction of the aminoketone moiety of the compound of formula (A1).

5. The process according to claim 4, wherein the aminoketone moiety is reduced in the presence of a rhodium or ruthenium-based catalyst.

6. The process according to claim 1, wherein the aminoketone moiety is reduced in the presence of a ruthenium-based catalyst.

7. The process according to claim 6, wherein the ruthenium-based catalyst is chosen from:

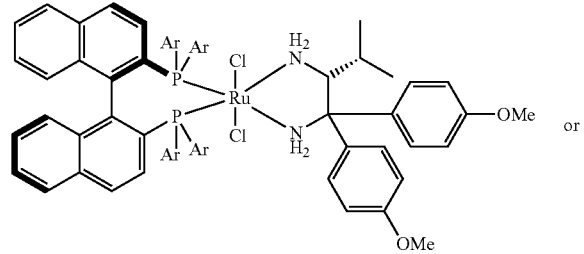 or

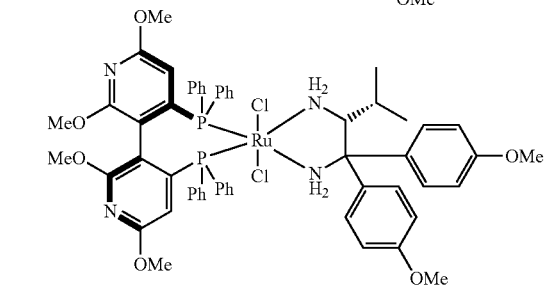

and wherein each Ar is the same and chosen from a phenyl or tolyl group.

8. The process according to claim 1, wherein the aminoketone moiety is reduced at a temperature ranging from room temperature to 75° C., under a pressure ranging from 3 to 30 bar, and in the presence of a base.

9. The process according to claim 8, wherein the aminoketone moiety is reduced at a temperature ranging from 65-70° C.

10. The process according to claim 8, wherein the base is potassium tertiary butoxide.

11. The process according to claim 1, wherein P¹ and P³ are the same or different, and each is independently chosen from a benzyl group or an allyl group.

12. The process according to claim 1, wherein both P¹ and P³ represent the same group.

13. The process according to claim 1, wherein groups P¹ and P³ are removed in a single step.

14. A process for preparing 5-(2-{[6-(2,2-difluoro-2-phenylethoxy)hexyl]amino}-1(R)-hydroxyethyl)-8-hydroxyquinolin-2(1H)-one or a pharmaceutically acceptable salt thereof, comprising:
  (i) preparing the compound of formula (Ap) according to claim 1, by reacting a compound of formula (VII), (VII)

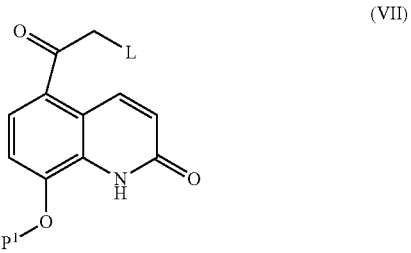

wherein L is a leaving group, with a compound of formula (X),

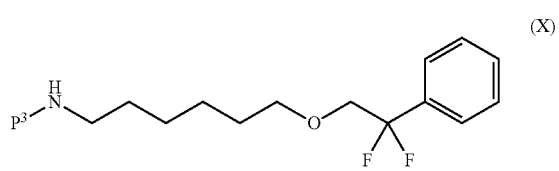

in the presence of a base, and then (ii) reducing and deprotecting the compound of formula (Ap).

15. The process according claim 14, wherein the group L is a halogen atom.

16. The process according to claim 14, wherein the base is chosen from triethylamine, diisopropylethylamine or potassium carbonate.

17. The process according to claim 1, further comprising treating 5-2-{[6-(2,2-difluoro-2-phenylethoxy)hexyl]amino}-1(R)-hydroxyethyl)-8-hydroxyquinolin-2(1H)-one with a pharmaceutically acceptable acid to form a pharmaceutically acceptable salt.

18. The process according to claim 17, wherein the pharmaceutically acceptable acid is naphthalene 1,5-disulphonic acid and the pharmaceutically acceptable salt is the napadisylate salt of formula (Ia):

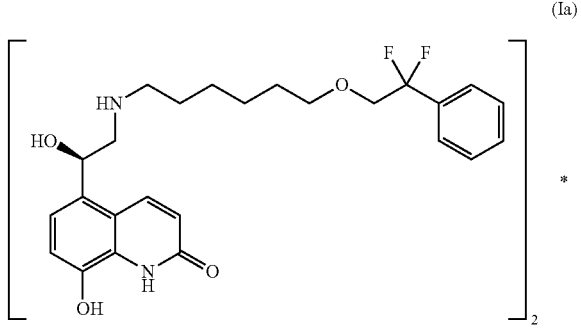

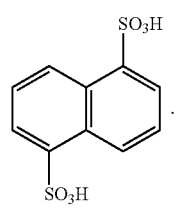

19. The process according to claim 1, wherein 5-(2-{[6-(2,2-difluoro-2-phenylethoxy)hexyl]amino}-1(R)-hydroxyethyl)-8-hydroxyquinolin-2(1H)-one is obtained in a form of a free base.

20. A compound of formula (A1) or a pharmaceutically acceptable salt thereof

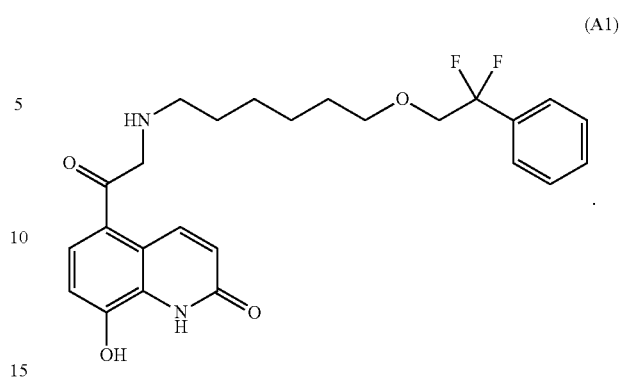

21. A process for preparing 5-(2-{[6-(2,2-difluoro-2-phenylethoxy)hexyl]amino}-1(R)-hydroxyethyl)-8-hydroxyquinolin-2(1H)-one or a pharmaceutically acceptable salt thereof, comprising:
reduction of the aminoketone moiety of the compound of formula (A1) according to claim 20, wherein the aminoketone moiety is reduced in the presence of a rhodium or ruthenium-based catalyst.

22. The process for preparing a compound of formula (A1) according to claim 20, comprising:
removal of protecting groups P¹ and P³ from a compound of formula (Ap) or a pharmaceutically acceptable salt thereof,

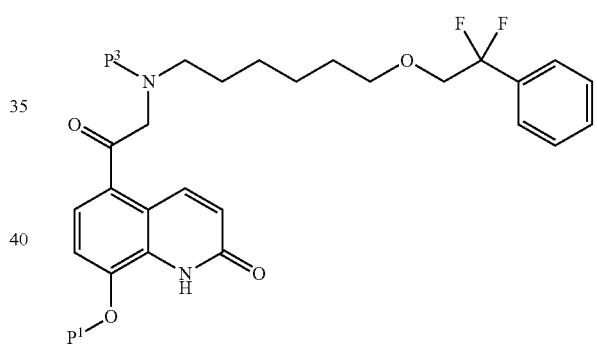

wherein P¹ represents hydroxy protecting group and P³ represents an amino protecting group, to give a compound of formula (A1) or a pharmaceutically acceptable salt thereof,

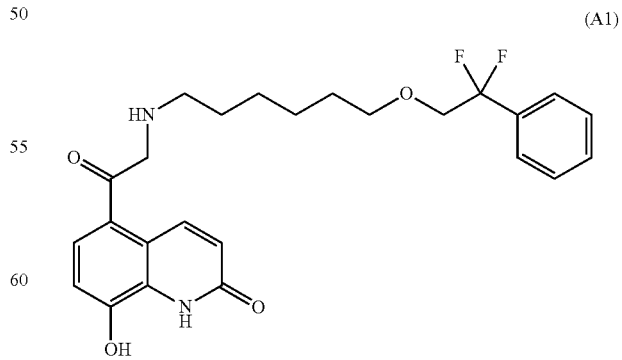

and
reduction of the aminoketone moiety of the compound of formula (A1).

23. The process according to claim 9, wherein the aminoketone moiety is reduced at a pressure of 25 bar.

24. The process according to claim 1, wherein $P^1$ and $P^3$ are represented by a benzyl group.

25. The process according claim 14, wherein the group L is represented by a bromine atom.

26. The process according to claim 16, wherein the base is triethylamine.

* * * * *